United States Patent
Krieger et al.

(10) Patent No.: US 9,820,744 B2
(45) Date of Patent: Nov. 21, 2017

(54) ANASTOMOSIS CLIPPING TOOL WITH HALF-LOOP CLIP

(71) Applicant: Children's National Medical Center, Washington, DC (US)

(72) Inventors: Axel Krieger, Washington, DC (US); Peter Kim, Washington, DC (US); Chris Wilson, Port Perry (CN); Stephen Abellera, Sacroborough (CN)

(73) Assignee: Children's National Medical Center, Washington, DC (US)

( * ) Notice: Subject to any disclaimer, the term of this patent is extended or adjusted under 35 U.S.C. 154(b) by 771 days.

(21) Appl. No.: 14/038,192

(22) Filed: Sep. 26, 2013

(65) Prior Publication Data

US 2014/0088621 A1 Mar. 27, 2014

Related U.S. Application Data

(60) Provisional application No. 61/705,875, filed on Sep. 26, 2012, provisional application No. 61/706,322, filed on Sep. 27, 2012.

(51) Int. Cl.
*A61B 17/08* (2006.01)
*A61B 17/11* (2006.01)
(Continued)

(52) U.S. Cl.
CPC .......... *A61B 17/11* (2013.01); *A61B 17/0401* (2013.01); *A61B 17/0469* (2013.01);
(Continued)

(58) Field of Classification Search
CPC . A61B 17/11; A61B 17/1152; A61B 17/0469; A61B 17/0401; A61B 17/0482;
(Continued)

(56) References Cited

U.S. PATENT DOCUMENTS 4,120,303 A * 10/1978 Villa-Massone ..... A01K 11/002
606/117
5,188,638 A 2/1993 Tzakis
(Continued)

FOREIGN PATENT DOCUMENTS

CN 101243985 A 8/2008
CN 102551820 A 7/2012
(Continued)

OTHER PUBLICATIONS

International Search Report and Written Opinion issued Jan. 3, 2014 in PCT/US13/61931.
(Continued)

*Primary Examiner* — Diane Yabut
*Assistant Examiner* — Erich Herbermann
(74) *Attorney, Agent, or Firm* — Oblon, McClelland, Maier & Neustadt, L.L.P.

(57) ABSTRACT

A tool to fasten tissue or to fasten a prosthetic to tissue includes a gripper to hold one or more tissue portions, a needle, an actuator to drive the needle, a fastener cartridge to store one or more tissue fasteners, a holder cartridge to store one or more holders, and a holder applier to secure one of the holders on one of the fasteners. The actuator drives the needle and the needle pulls a first fastener from the fastener cartridge. The actuator drives the needle through the one or more tissue portions held by the gripper to form a hole in the tissue portions. The needle pulls a leading portion of the first fastener through the hole without a trailing portion of the first fastener being pulled through the hole. The holder applier secures a first holder from the holder cartridge onto the leading portion of the first fastener.

17 Claims, 44 Drawing Sheets

Needle Advancer Arm Actuation

(51) Int. Cl.
  *A61B 17/04* (2006.01)
  *A61B 17/115* (2006.01)
  *A61B 17/06* (2006.01)
  *A61B 17/29* (2006.01)
(52) U.S. Cl.
  CPC ...... *A61B 17/0482* (2013.01); *A61B 17/0487* (2013.01); *A61B 17/1152* (2013.01); *A61B 17/06* (2013.01); *A61B 2017/0404* (2013.01); *A61B 2017/0409* (2013.01); *A61B 2017/0417* (2013.01); *A61B 2017/0496* (2013.01); *A61B 2017/06042* (2013.01); *A61B 2017/1107* (2013.01); *A61B 2017/1132* (2013.01); *A61B 2017/1135* (2013.01); *A61B 2017/1139* (2013.01); *A61B 2017/2927* (2013.01)
(58) Field of Classification Search
  CPC ............ A61B 17/0487; A61B 17/06; A61B 17/128–17/1285; A61B 17/07292; A61B 2017/1135; A61B 2017/0417; A61B 2017/1139; A61B 2017/1107; A61B 2017/0404; A61B 2017/2927; A61B 2017/1132; A61B 2017/0496; A61B 2017/0409; A61B 17/0483; A61B 17/0485; A61B 17/062; A61B 2017/06009; A61B 2017/06014; A61B 2017/06019; A61B 2017/06061; A61B 2017/06071; A61B 2017/06076; A61B 2017/0608; A01K 11/00; A01K 11/001; A01K 11/002
  USPC ........ 606/142–143, 151–156, 139, 104, 117; 40/301–303; 119/655, 862
  See application file for complete search history.

(56) References Cited

U.S. PATENT DOCUMENTS

| | | |
|---|---|---|
| 5,437,681 A | 8/1995 | Meade et al. |
| 5,540,705 A | 7/1996 | Meade et al. |
| 5,665,096 A | 9/1997 | Yoon |
| 5,665,109 A | 9/1997 | Yoon |
| 5,759,188 A | 6/1998 | Yoon |
| 5,860,992 A | 1/1999 | Daniel et al. |
| 5,954,733 A | 9/1999 | Yoon |
| 6,358,258 B1 | 3/2002 | Arcia et al. |
| 6,425,887 B1 | 7/2002 | McGuckin et al. |
| 6,626,916 B1 | 9/2003 | Yeung et al. |
| 6,719,763 B2 | 4/2004 | Chung et al. |
| 6,755,843 B2 | 6/2004 | Chung et al. |
| 6,923,819 B2 | 8/2005 | Meade et al. |
| 7,029,481 B1 | 4/2006 | Burdulis, Jr. et al. |
| 7,326,203 B2 * | 2/2008 | Papineau ......... A61B 17/32002 606/104 |
| 7,862,572 B2 | 1/2011 | Meade et al. |
| 7,993,354 B1 | 8/2011 | Brecher et al. |
| 8,066,737 B2 | 11/2011 | Meade et al. |
| 8,100,922 B2 | 1/2012 | Griffith |
| 8,123,764 B2 | 2/2012 | Meade et al. |
| 2003/0032929 A1 | 2/2003 | McGuckin, Jr. |
| 2003/0221344 A1* | 12/2003 | Volk ..................... A01K 11/00 40/301 |
| 2005/0015101 A1* | 1/2005 | Gibbens, III ...... A61B 17/0482 606/144 |
| 2006/0020167 A1 | 1/2006 | Sitzmann |
| 2006/0178560 A1 | 8/2006 | Saadat et al. |
| 2007/0233164 A1 | 10/2007 | Bender et al. |
| 2008/0065111 A1 | 3/2008 | Blumenkranz et al. |
| 2008/0097391 A1 | 4/2008 | Feinberg et al. |
| 2008/0275472 A1 | 11/2008 | Yossepowitch et al. |
| 2009/0020584 A1* | 1/2009 | Soltz .................. A61B 17/0644 227/175.1 |
| 2009/0093824 A1 | 4/2009 | Hasan et al. |
| 2010/0152751 A1 | 6/2010 | Meade et al. |
| 2011/0088295 A1* | 4/2011 | Ibsen ................... A01K 11/001 40/301 |
| 2012/0089182 A1 | 4/2012 | Page et al. |
| 2012/0095458 A1* | 4/2012 | Cybulski ............ A61B 1/00071 606/41 |

FOREIGN PATENT DOCUMENTS

| | | |
|---|---|---|
| EP | 1 584 294 A2 | 10/2005 |
| EP | 2 119 412 A1 | 11/2009 |
| JP | 2003-052702 A | 2/2003 |
| JP | 2005-296644 A | 10/2005 |
| WO | WO 96/20647 A1 | 7/1996 |
| WO | WO 2010/138580 A2 | 12/2010 |
| WO | WO 2010/138582 A3 | 12/2010 |
| WO | WO 2011/116379 A2 | 9/2011 |

OTHER PUBLICATIONS

Extended European Search Report issued Jun. 21, 2016 in Patent Application No. 13840746.5.
Communication pursuant to Rules 70(2) and 70a(2) EPC issued Jul. 8, 2016 in European Patent Application No. 13840746.5.
Combined Chinese Office Action and Search Report issued Oct. 8, 2016 in Patent Application No. 201380059440.8 (with English language translation).
Office Action dated Jul. 4, 2017 in corresponding Japanese Application No. 2015-534658 (with Machine-Generated English Translation).
Office Action dated Jul. 14, 2017 in corresponding Chinese Application No. 2013-80059440.8 (with English Translation).

* cited by examiner

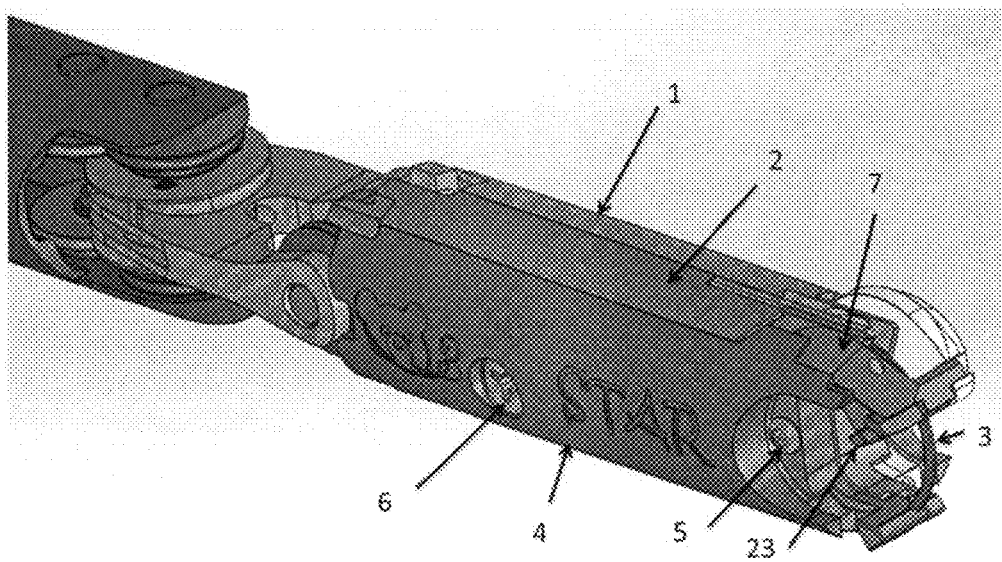
Figure 1: Clipping Tool Tip Isometric View #1
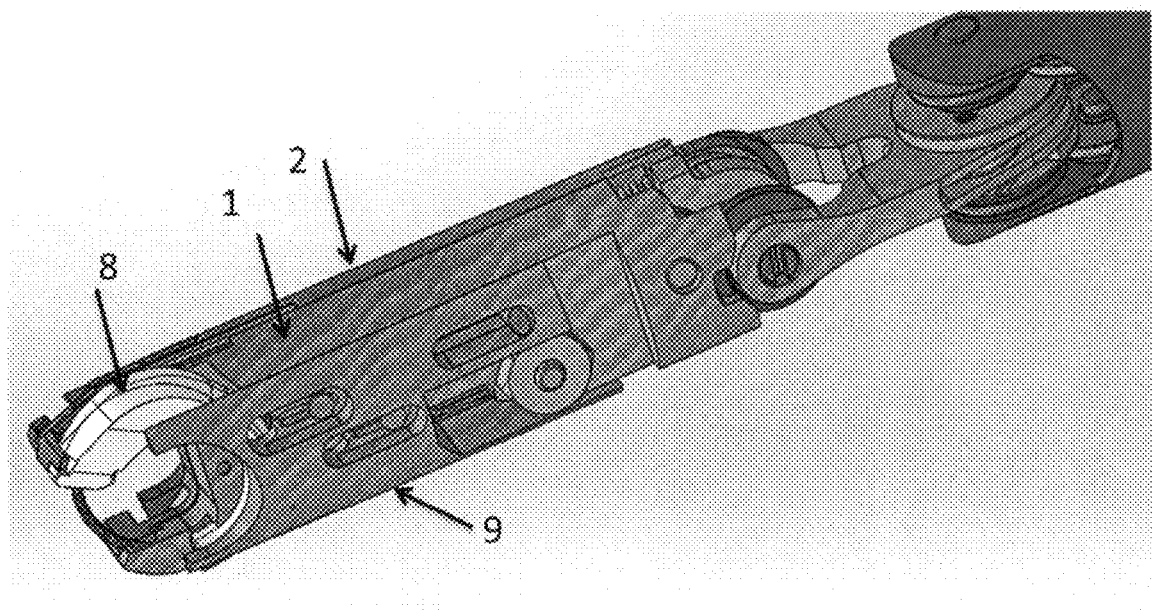
Figure 2: Clipping Tool Tip Isometric View #2

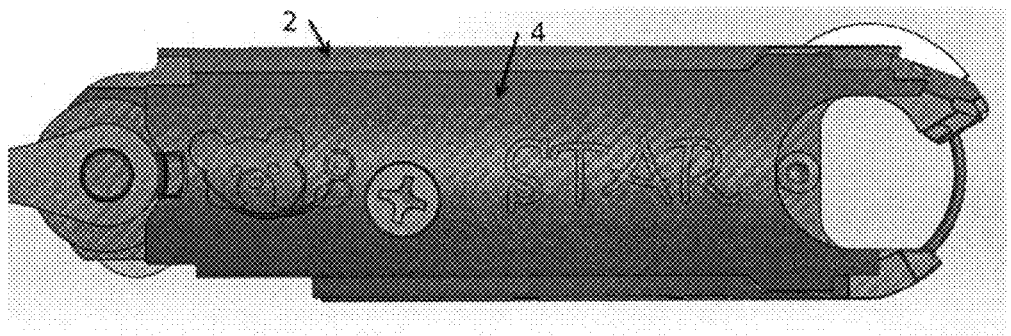
Figure 3: Clipping Tool Tip Side View #1
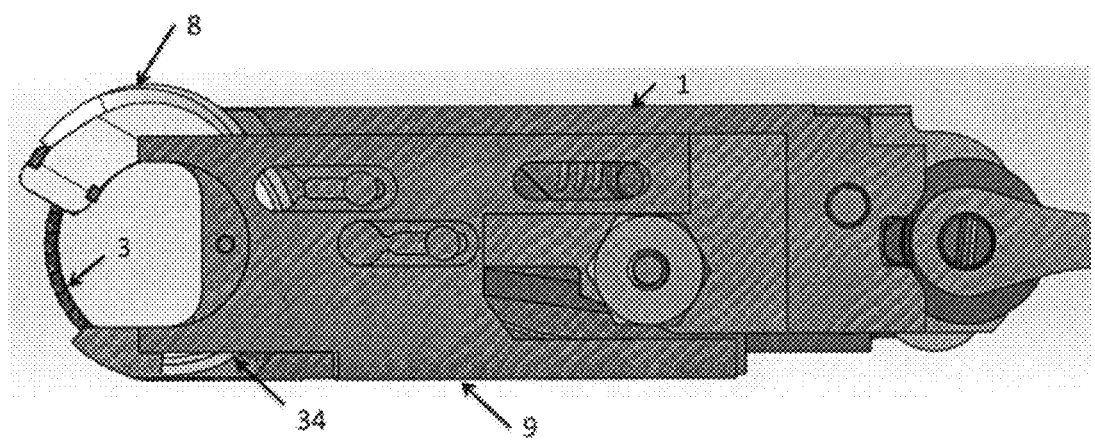
Figure 4: Clipping Tool Tip Side View #2

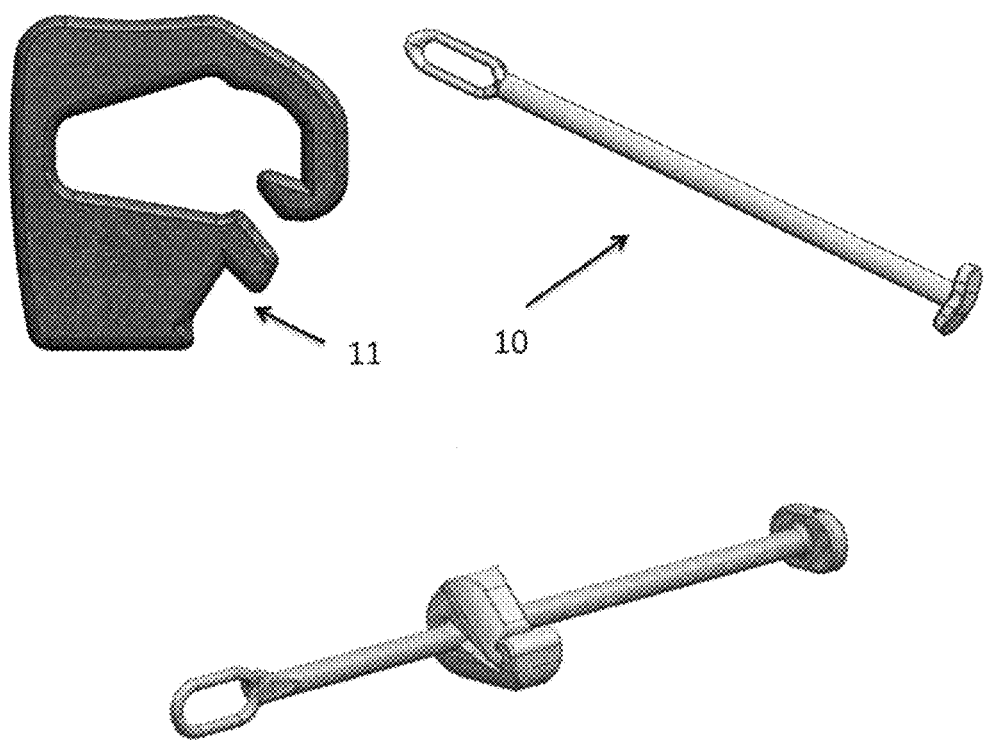
Figure 5: Clip and Clasp

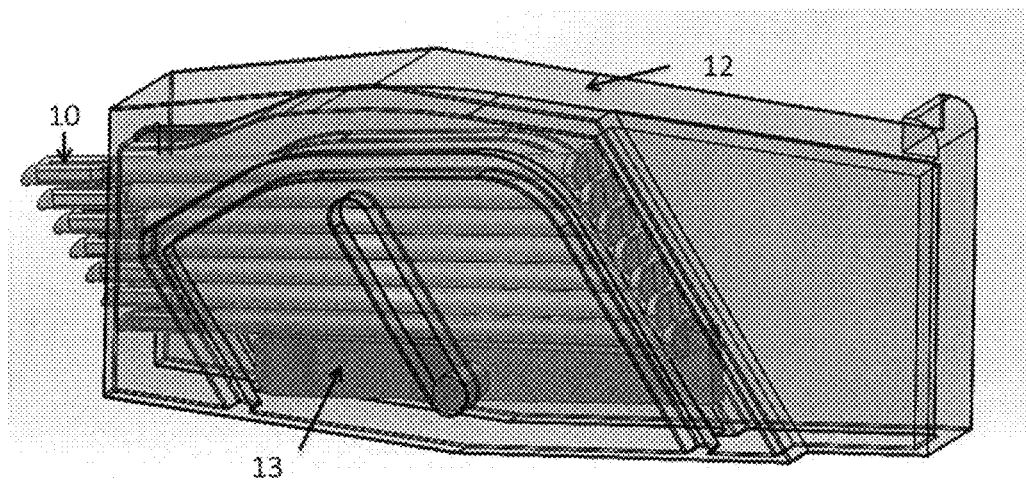
Figure 6: Clip Cartridge Loading
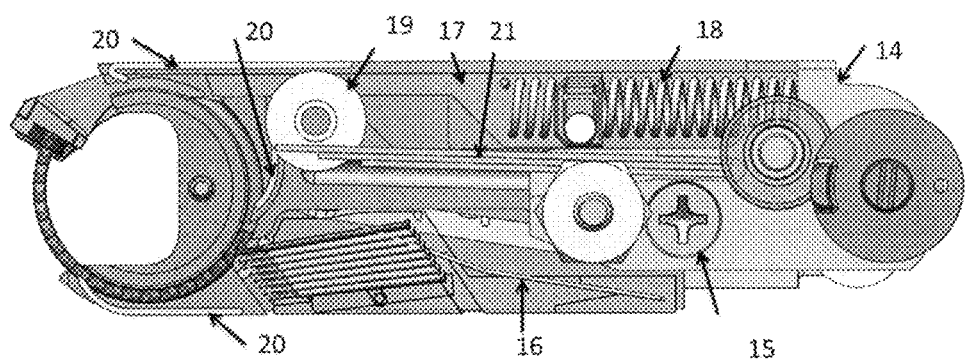
Figure 7: Clipping Tool Tip Cross-Sectional View #1

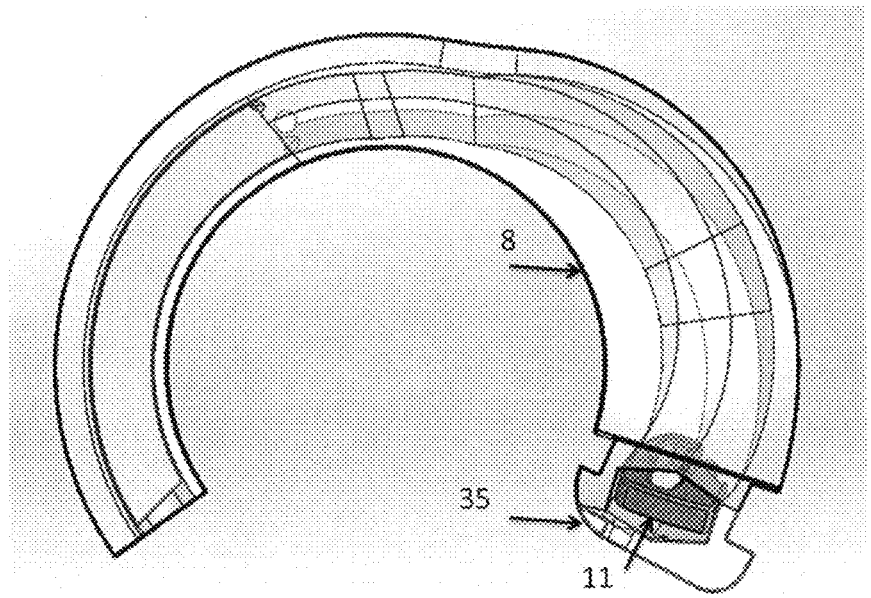
Figure 8: Clasp Cartridge
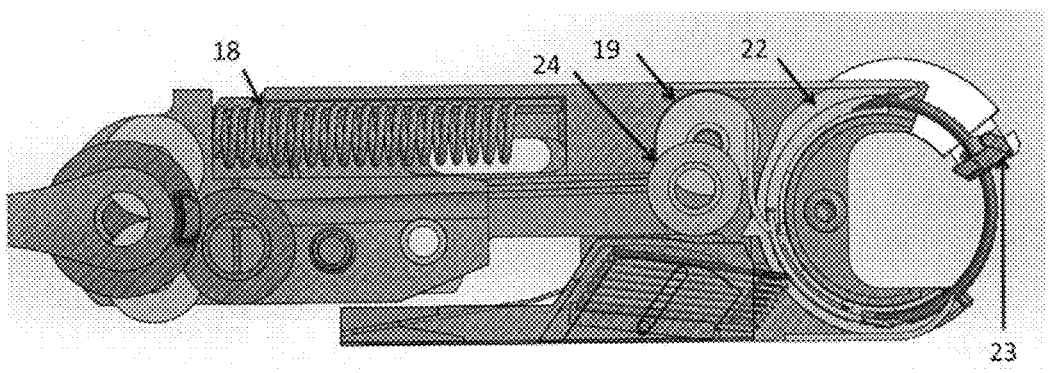
Figure 9: Clipping Tool Tip Cross-Sectional View #2

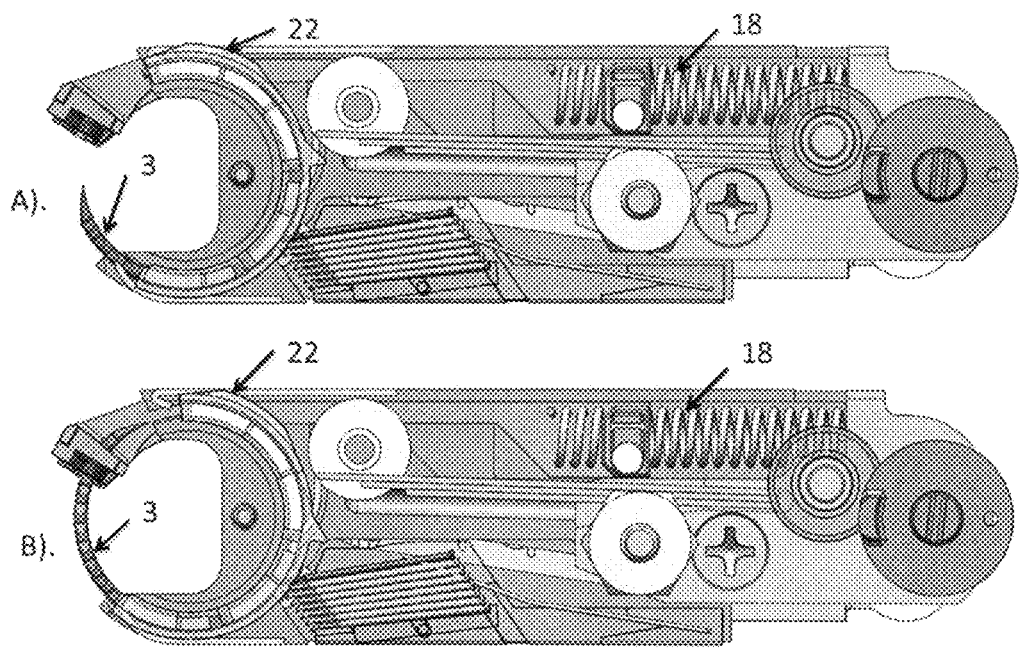
Figure 10: Needle Advancer Arm Actuation
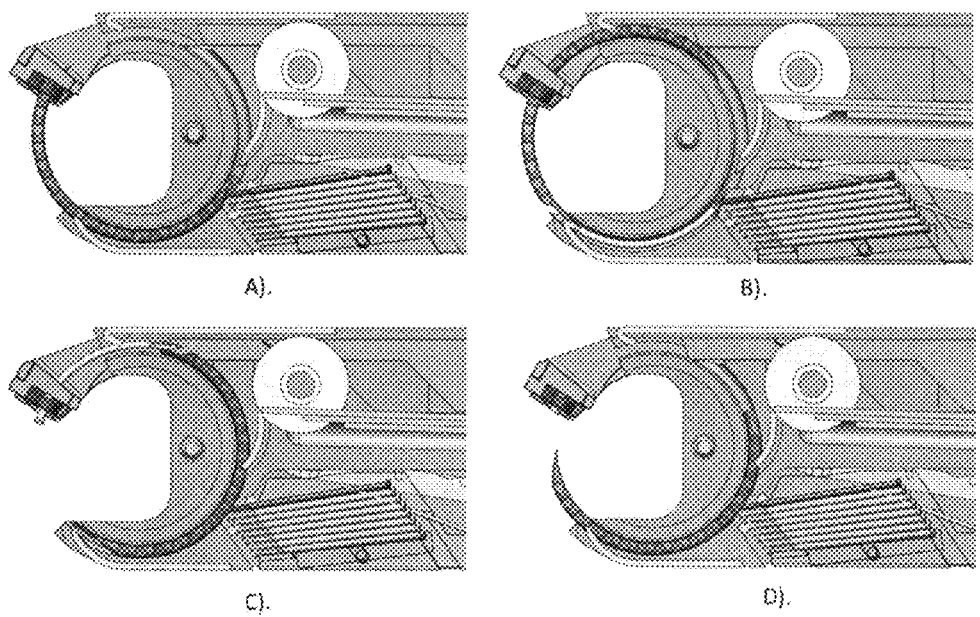
Figure 11: Needle Advancement Sequence

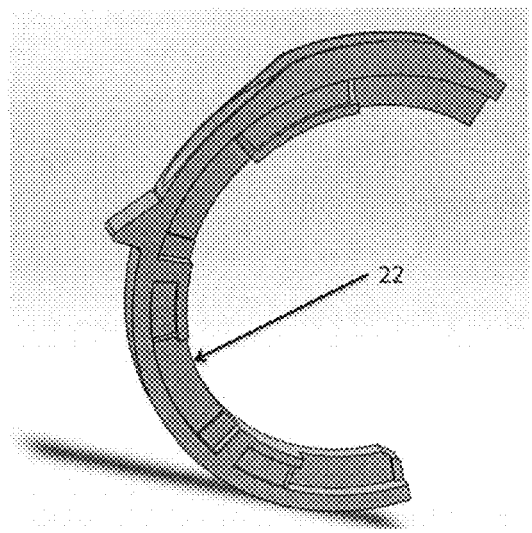
Figure 12: Needle Advancer Arm
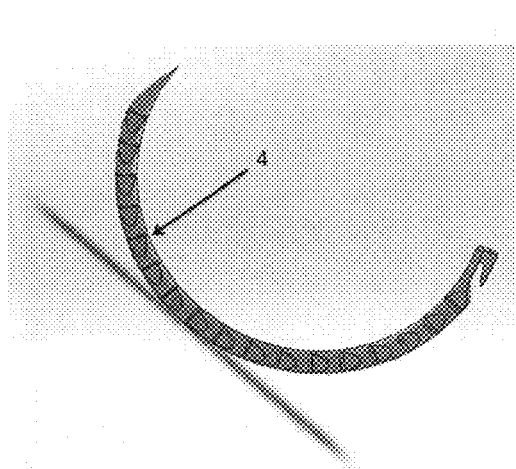
Figure 13: Needle Side View
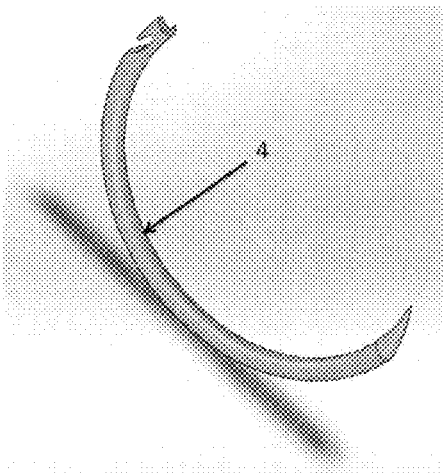
Figure 14: Needle Isometric View

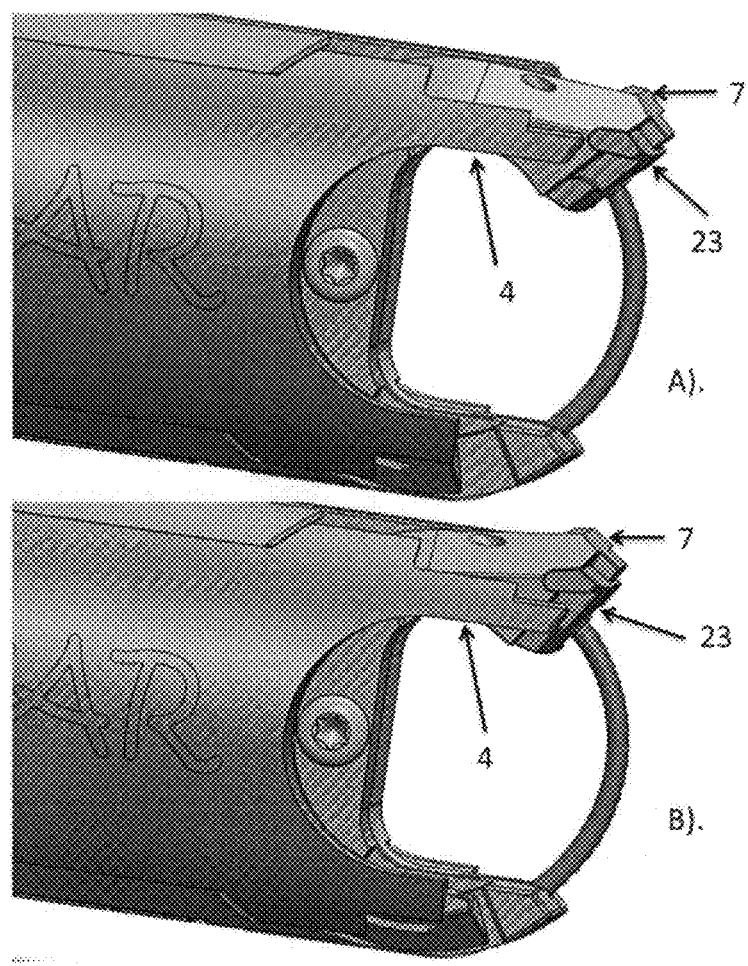
Figure 15: Clasp Closing Actuator

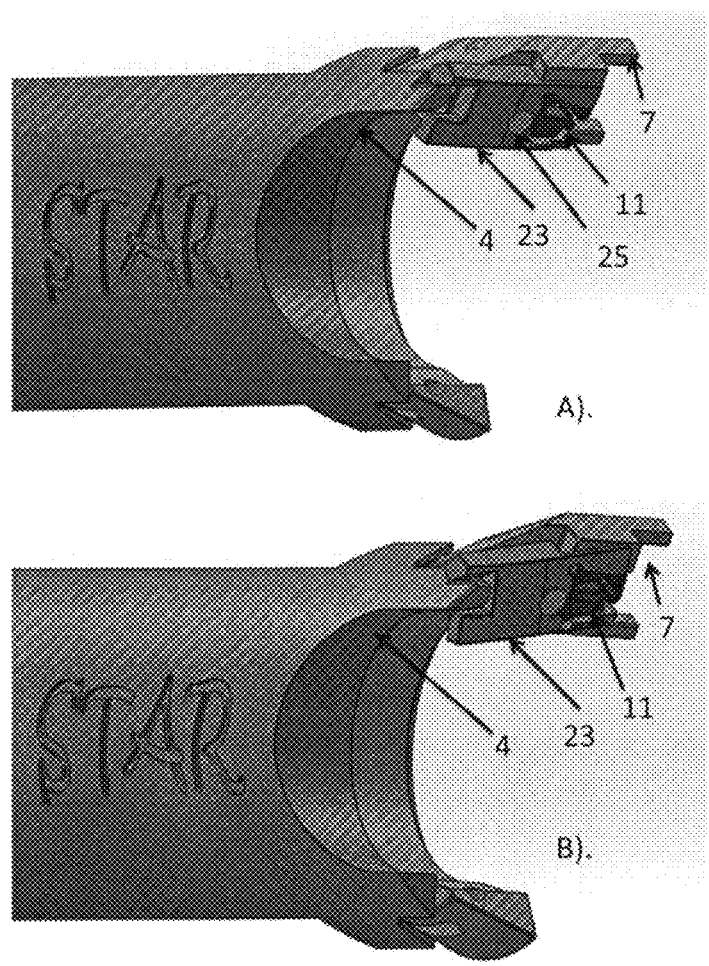
Figure 16: Clasp Closing

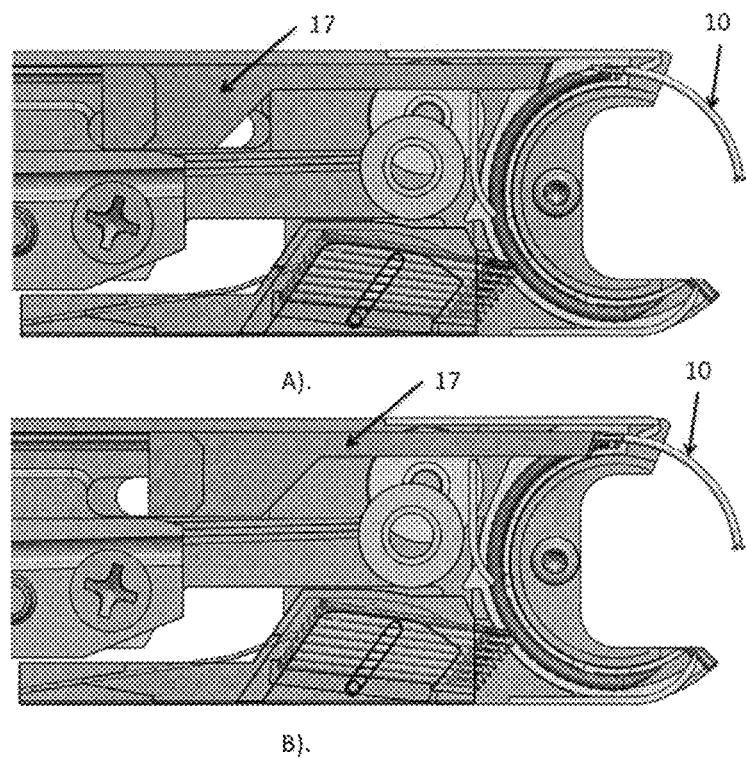
Figure 17: Clip Cutting
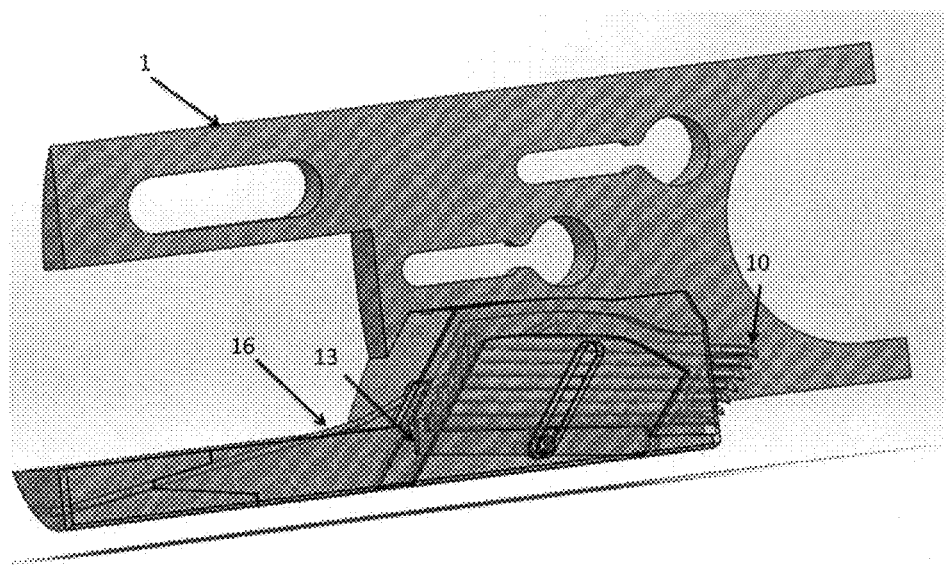
Figure 18: Clip Cartridge Advancement Mechanism (Top View)

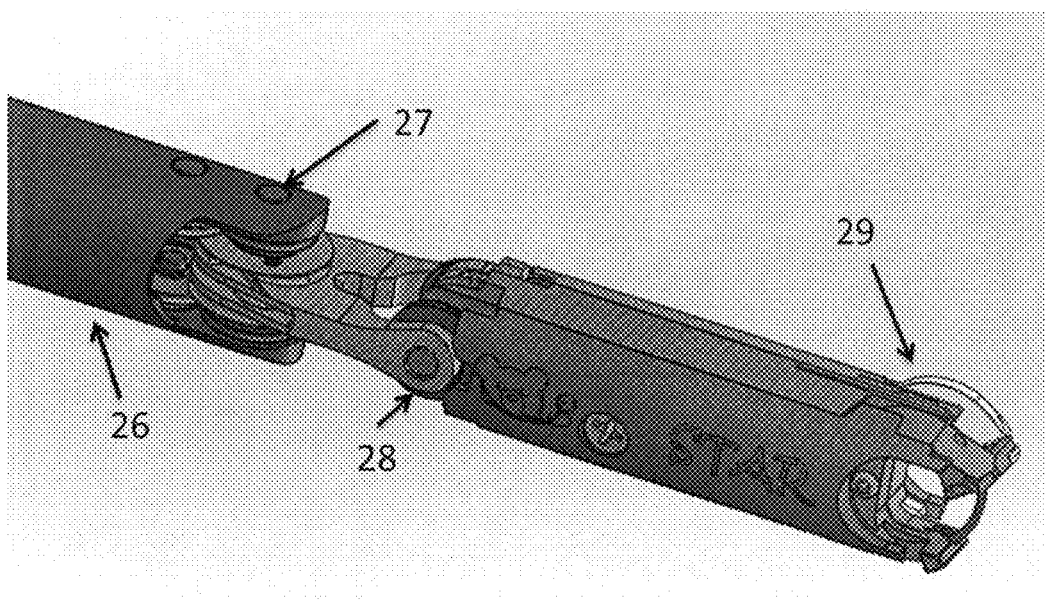
Figure 19: Example of Apparatus Variation with 2 positioning Degrees of Freedom (Pitch and Roll) on Shaft Figure 20: Operations Flow for the Tool Tip
Step 1: Forcep closed for entry through trochar.
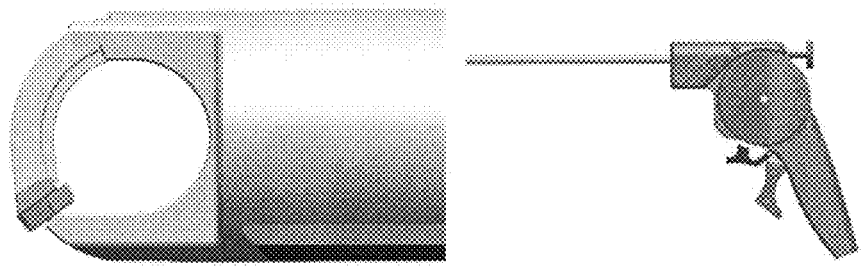
Step 2: Forcep opens.
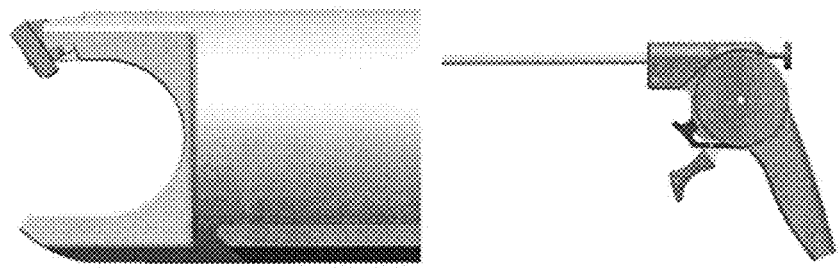
Step 3: : Tool tip positions around first lumen.

Figure 20: Operations Flow for the Tool Tip (continued)
Step 4: Forcep closes on first lumen.
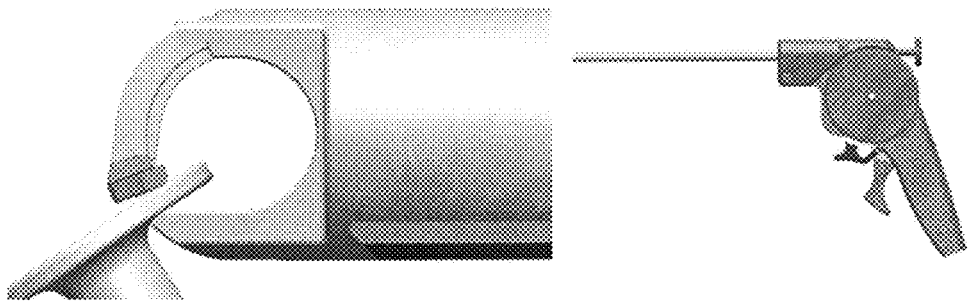
Step 5: Needle advances through first lumen.
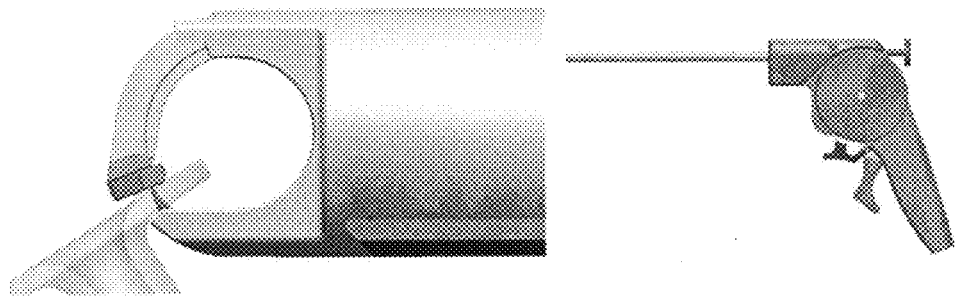
Step 6: Forcep opens.
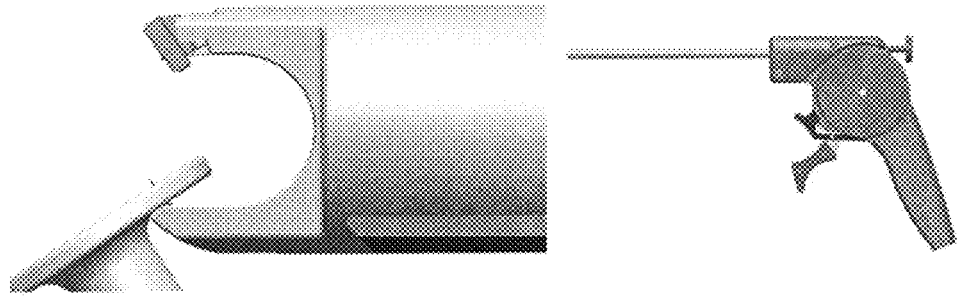

Figure 20: Operations Flow for the Tool Tip (continued)
Step 7: Tool tip positions with second lumen.
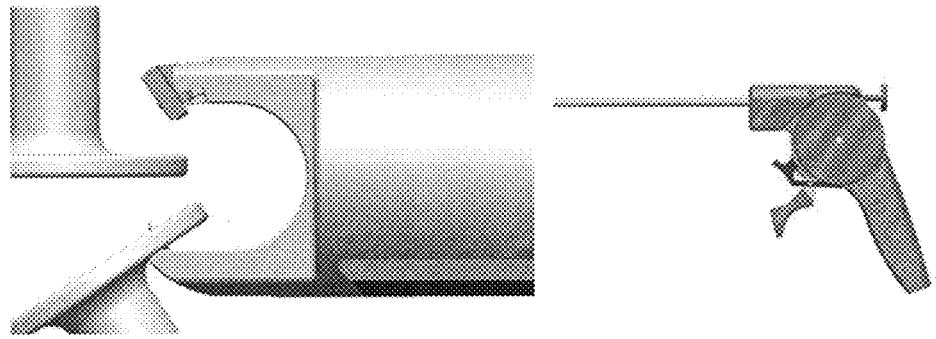
Step 8: Forcep closes on second lumen.
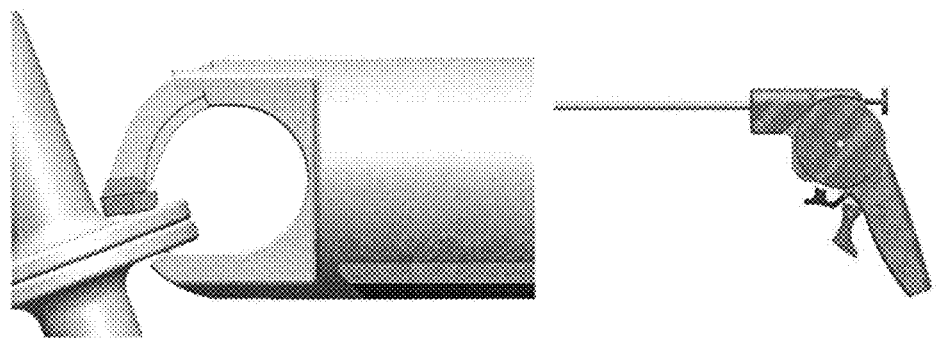
Step 9: Needle advances through second lumen.
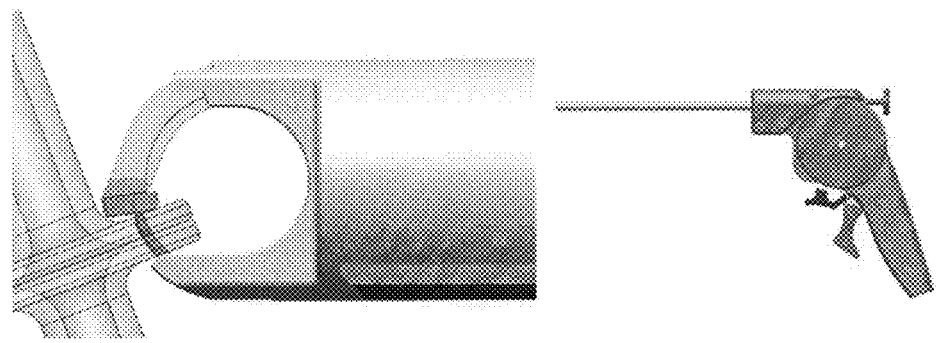

Figure 20: Operations Flow for the Tool Tip (continued)
Step 10: Needle advance pulls clip through lumina.
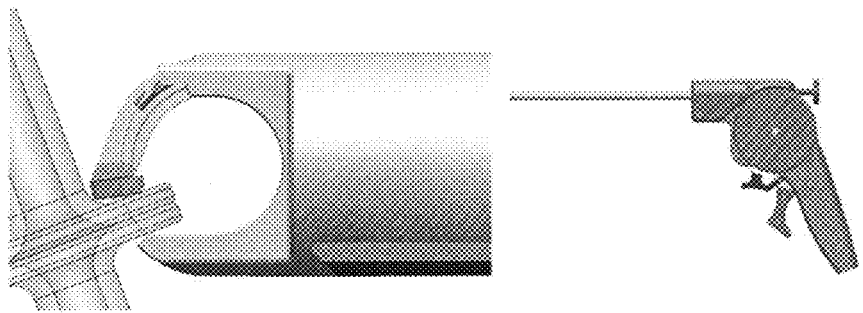
Step 11: Needle and forcep controls are locked together.
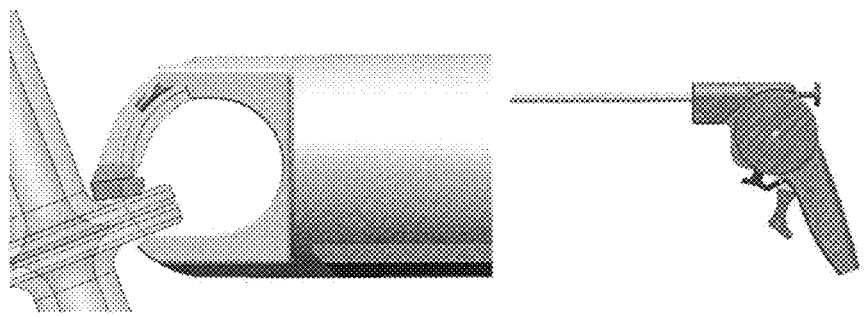
Step 12: Needle advance and forcep move together to bring clip to upper jaw.
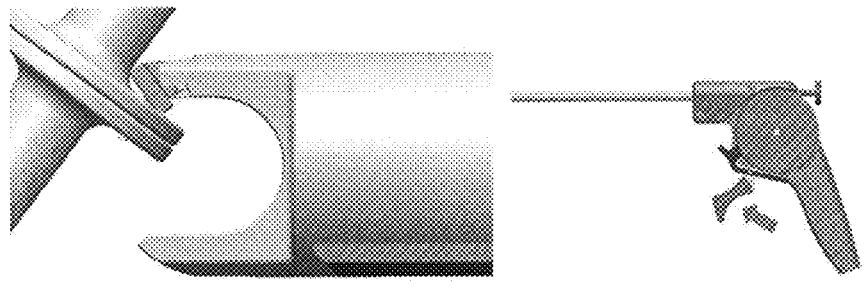

Figure 20: Operations Flow for the Tool Tip (continued)
Step 13: Needle and forcep continue motion closing the clasp on the clip.
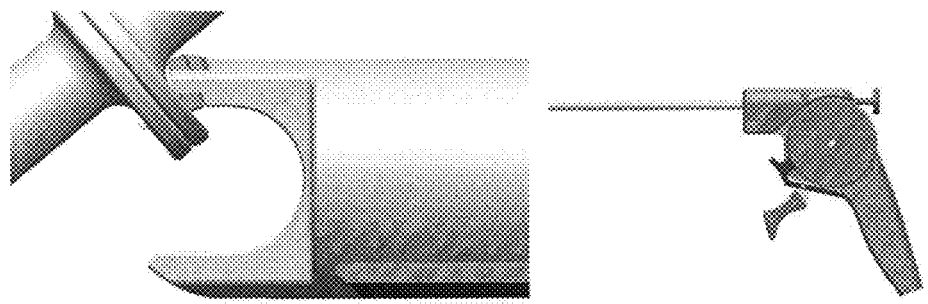
Step 14: Clip loop shear mechanism.
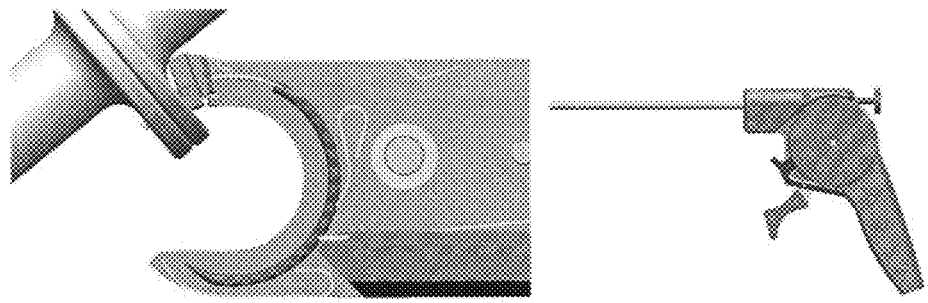
Step 15: Clip loop shear mechanism is activated.
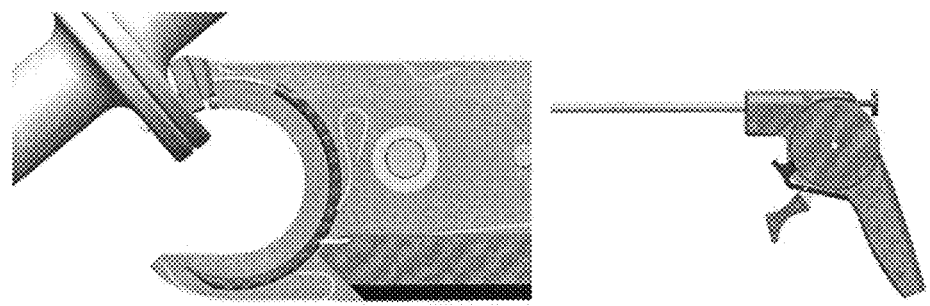

Figure 20: Operations Flow for the Tool Tip (continued)
Step 16: Tool tip retracts from site allowing compressed lumen to expand to specified clip length.
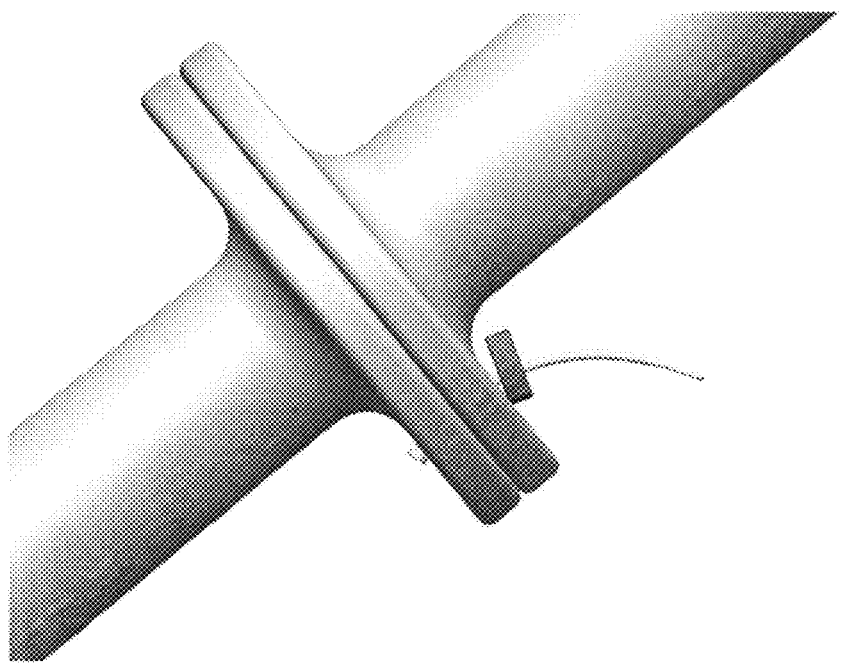

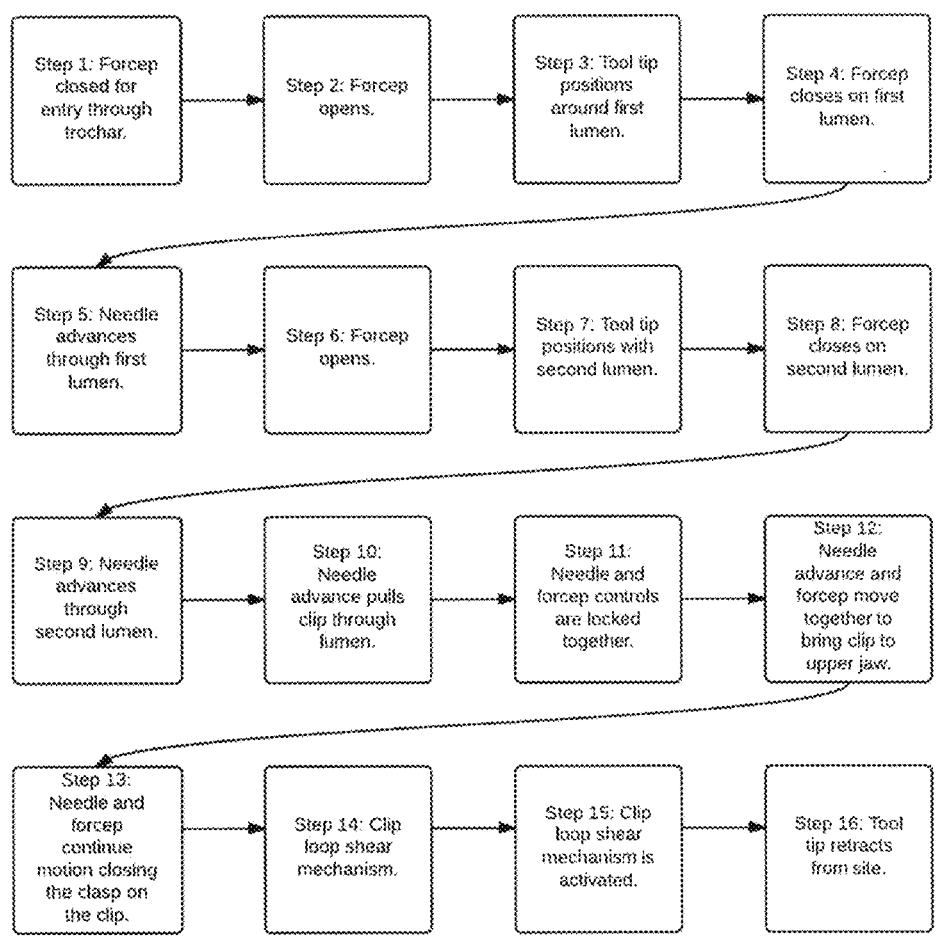
Figure 21: Sequence of Operation for the Clipping Method

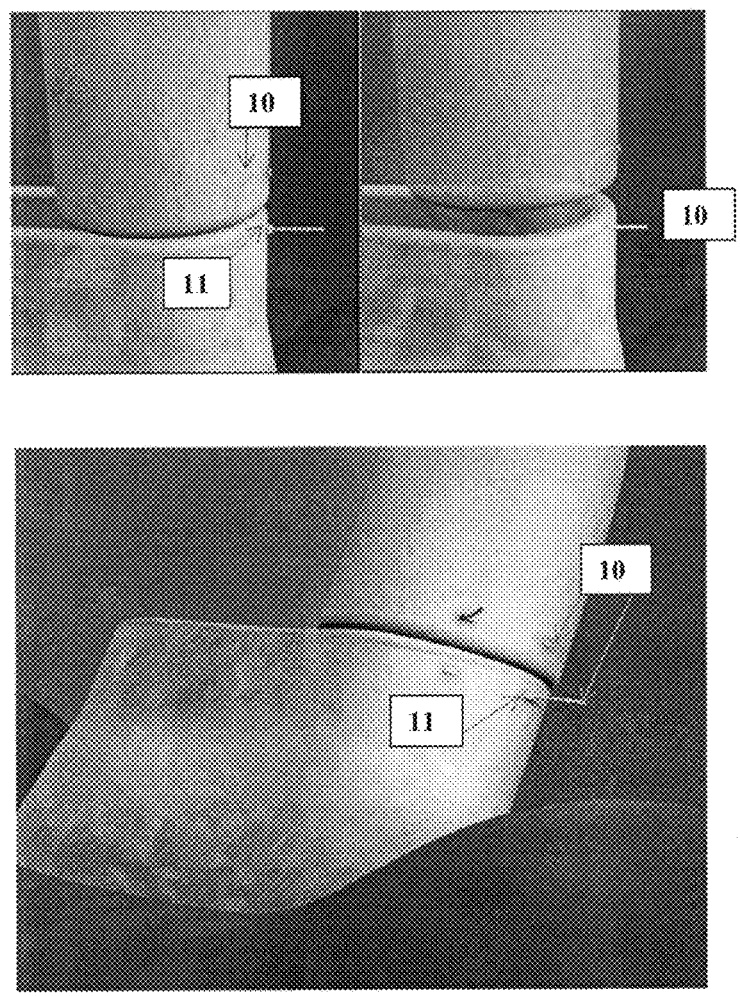
Figure 22: Half-loop Clip and Clasp After Deployment in Tissue

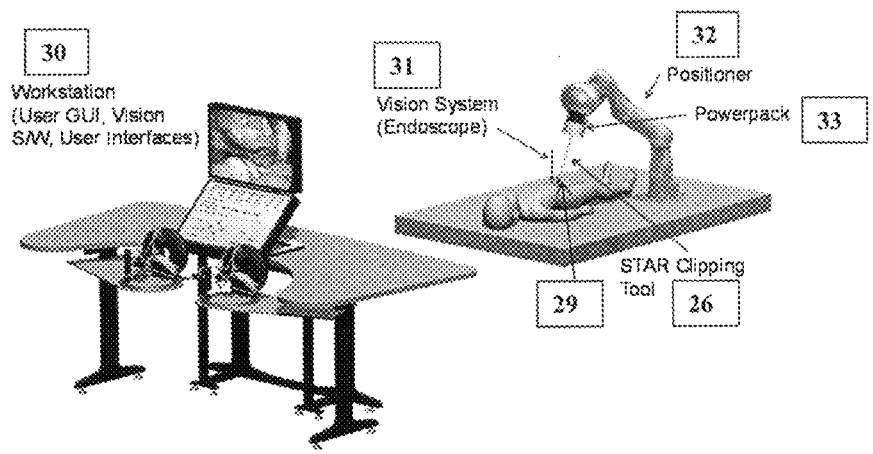
Figure 23: Overview of the Clipping System Robotic Embodiment
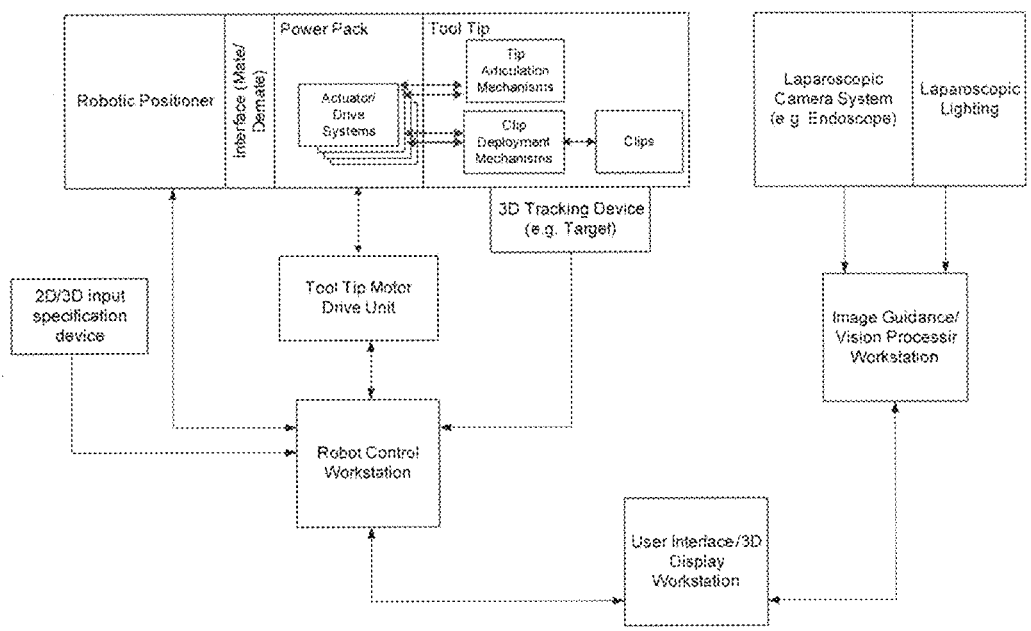
Figure 24: System Architechture and Workstation/Robotic Workcell of the Shared Image-guided System.

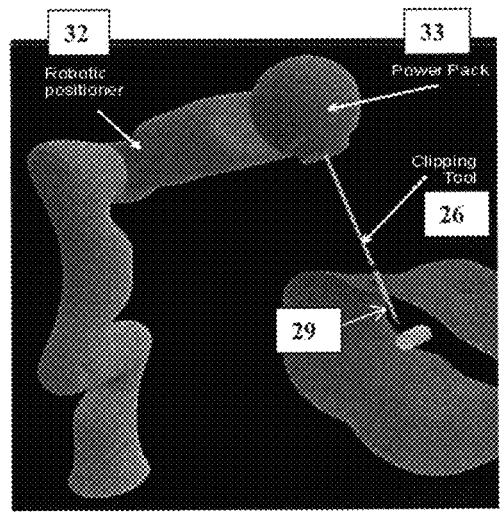
Figure 25: Robot-driven Embodiment of the Clipping Apparatus
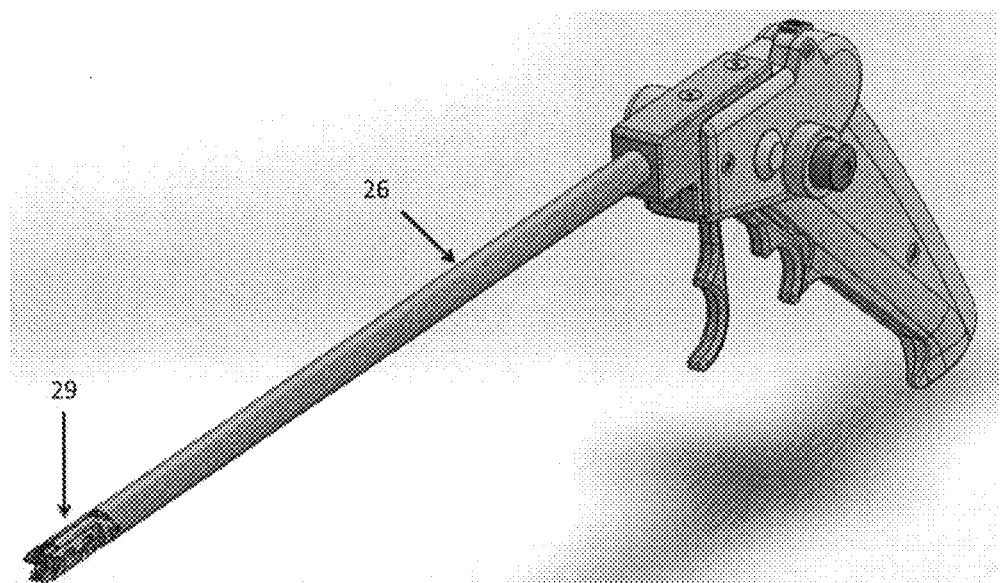
Figure 26: Manual/Handheld Embodiment of the Clipping Apparatus

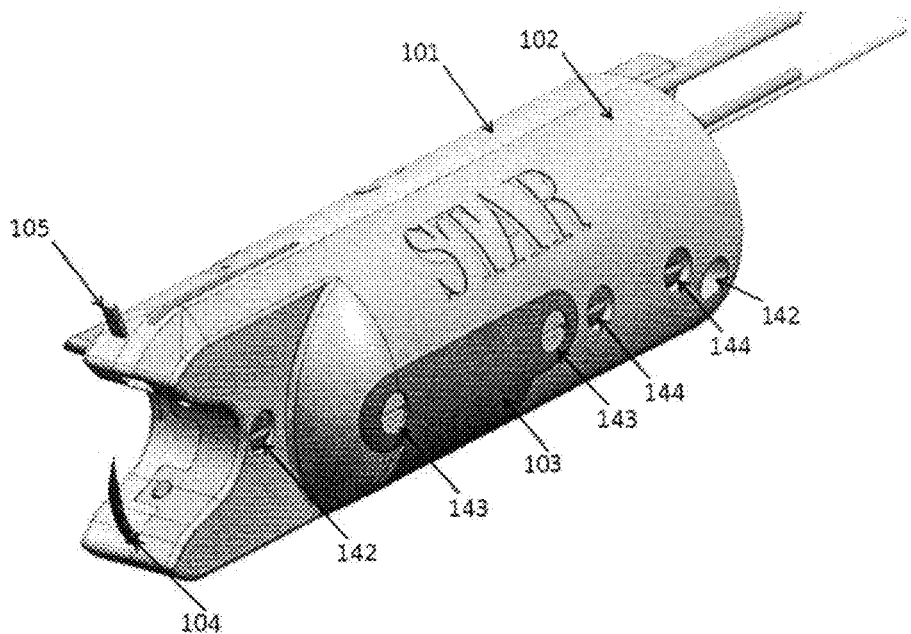
Figure 27: Clipping Tool Tip Isometric View #1
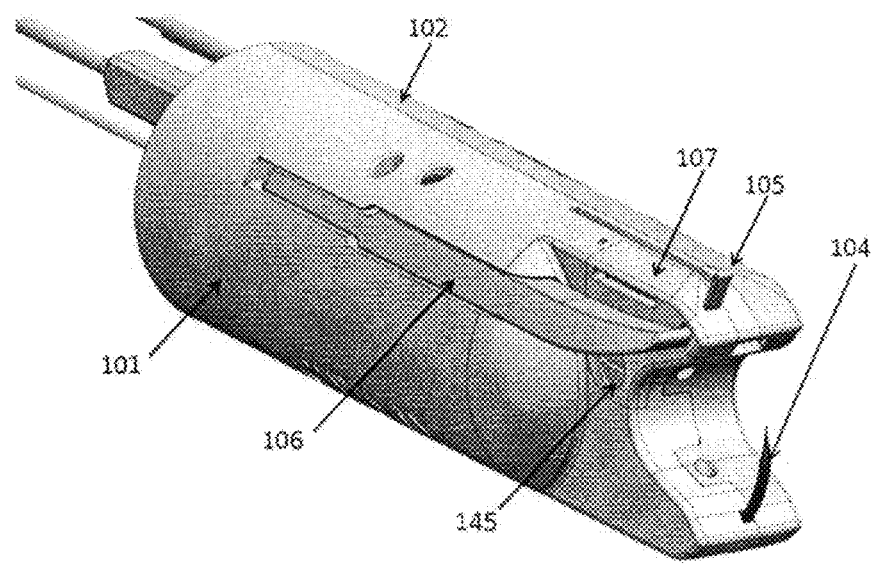
Figure 28: Clipping Tool Tip Isometric View #2

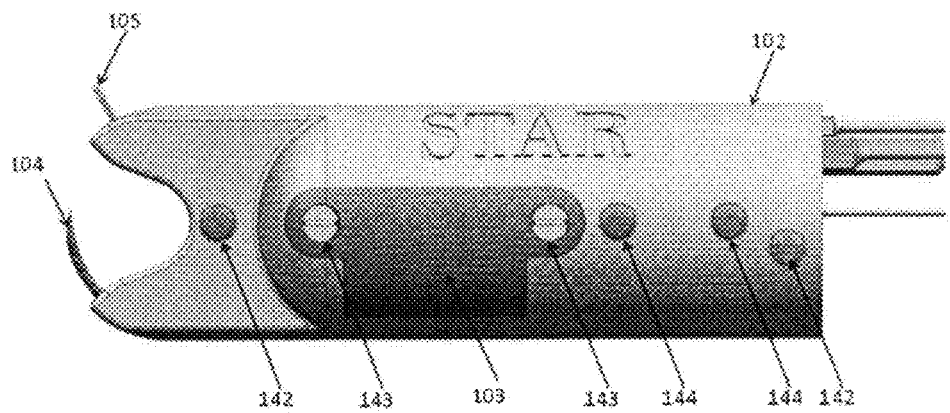
Figure 29: Clipping Tool Tip Side View #1
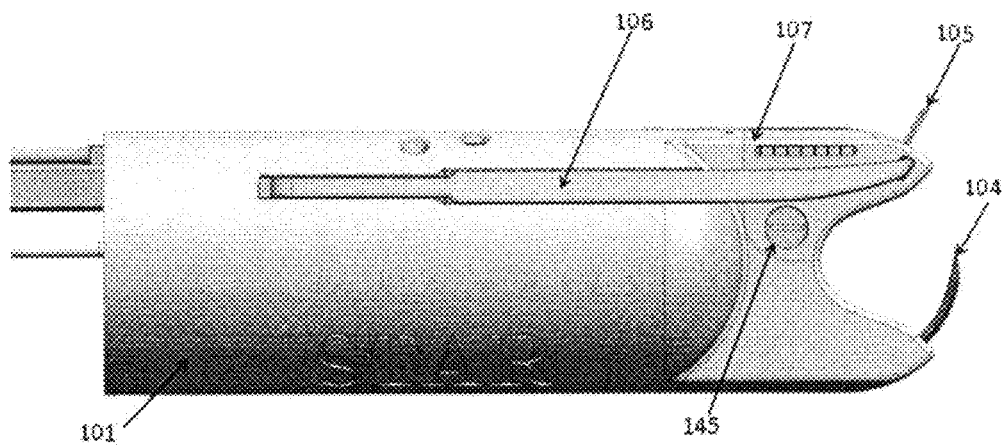
Figure 30: Clipping Tool Tip Side View #2

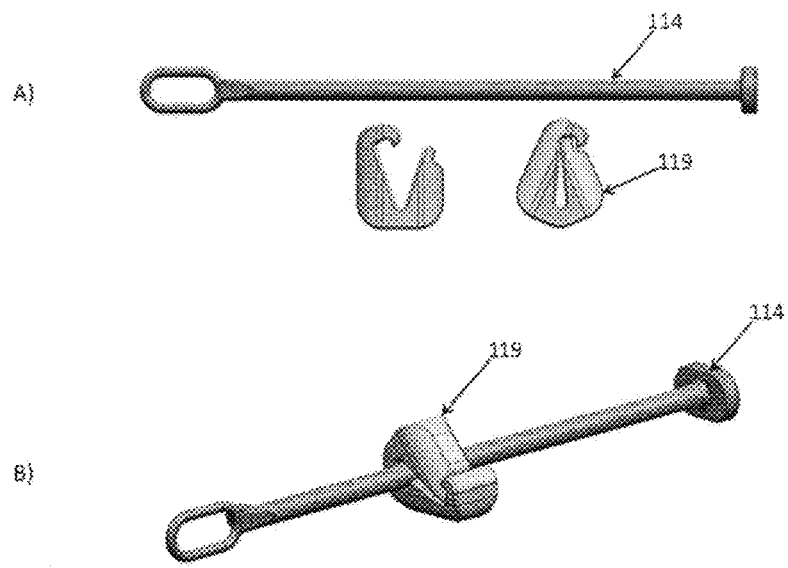
Figure 31: Clip and Clasp
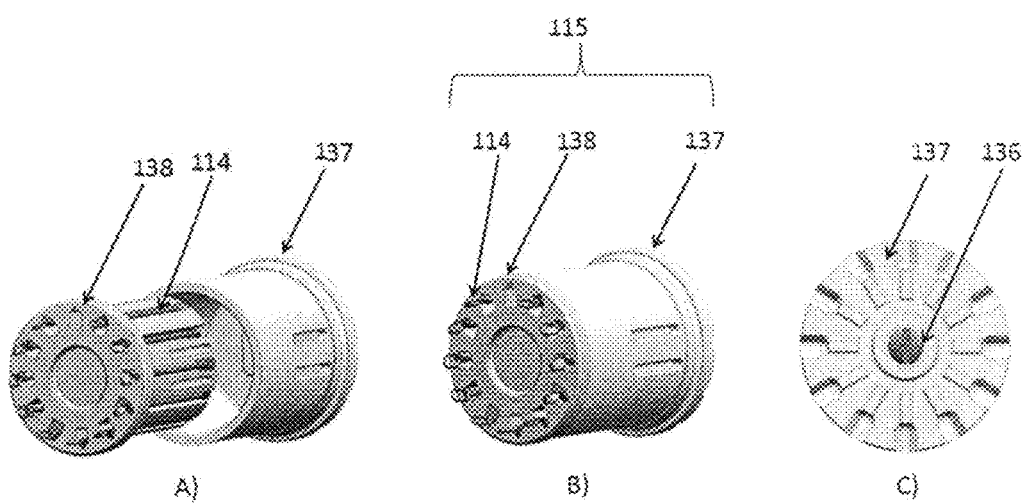
Figure 32: Clip Cartridge Loading

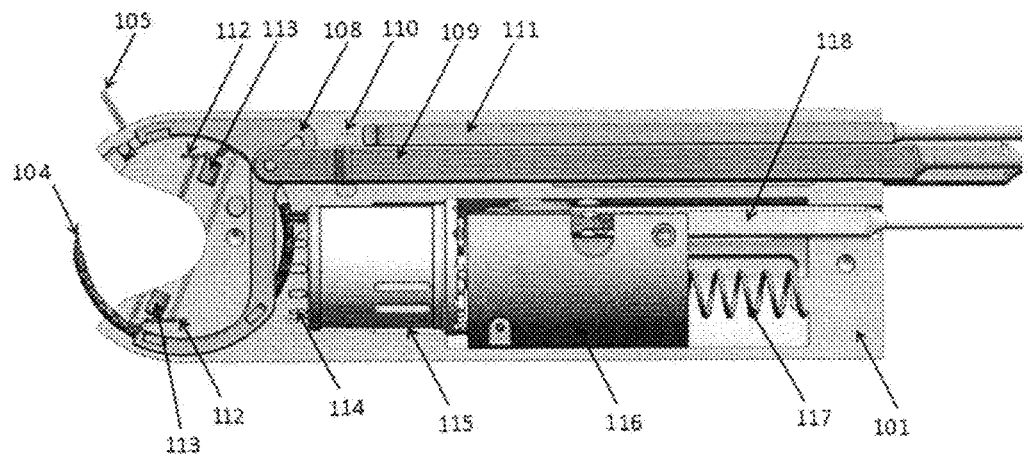
Figure 33: Clipping Tool Tip Cross-Sectional View #1
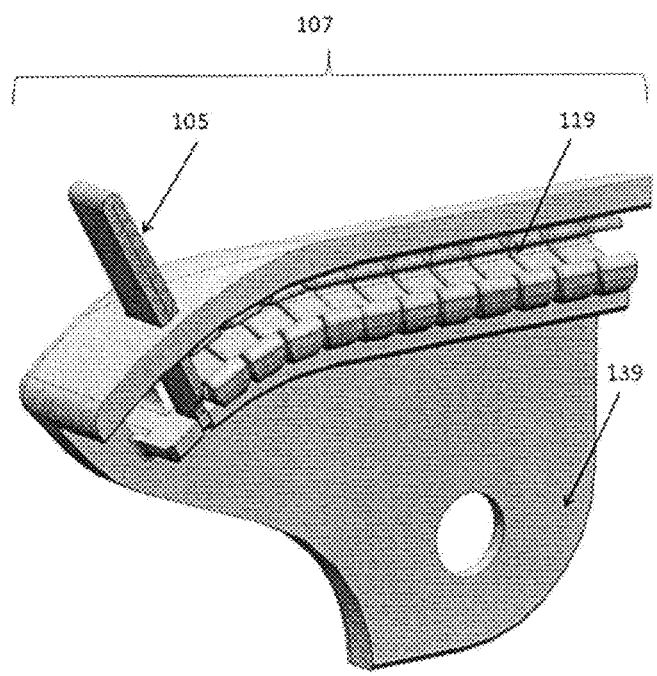
Figure 34: Clasp Cartridge

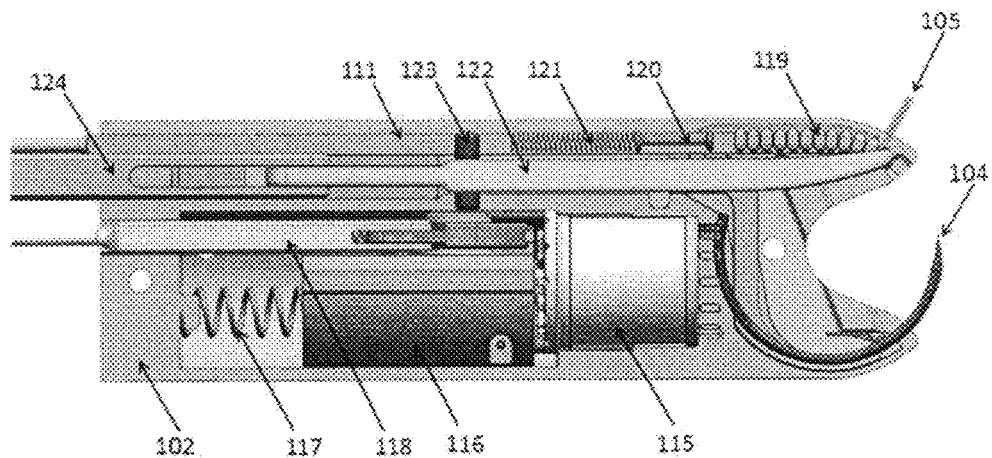
Figure 35: Clipping Tool Tip Cross-Sectional View #2
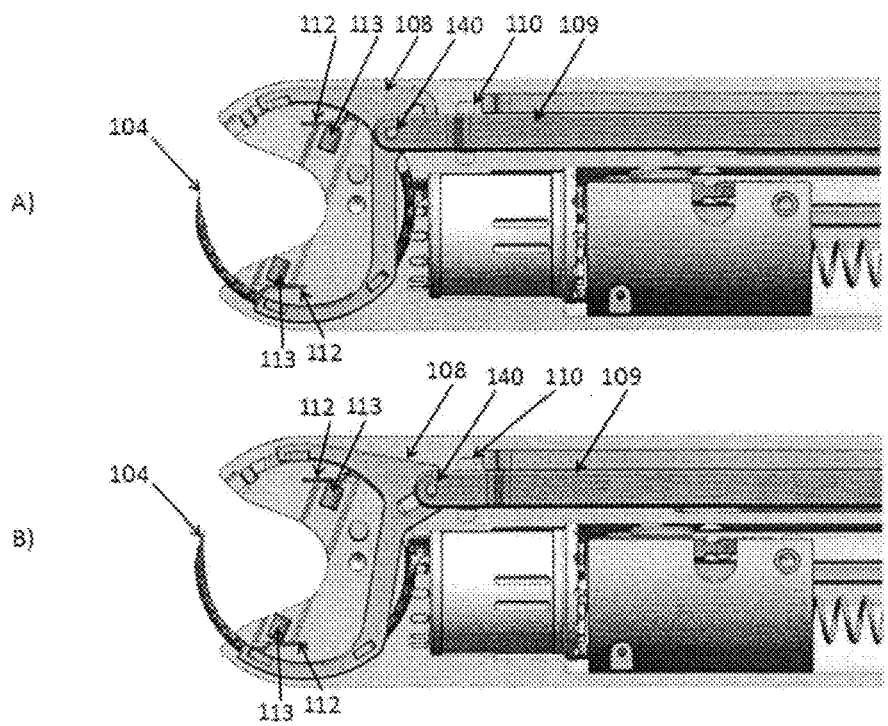
Figure 36: Needle Advancer Arm Actuation

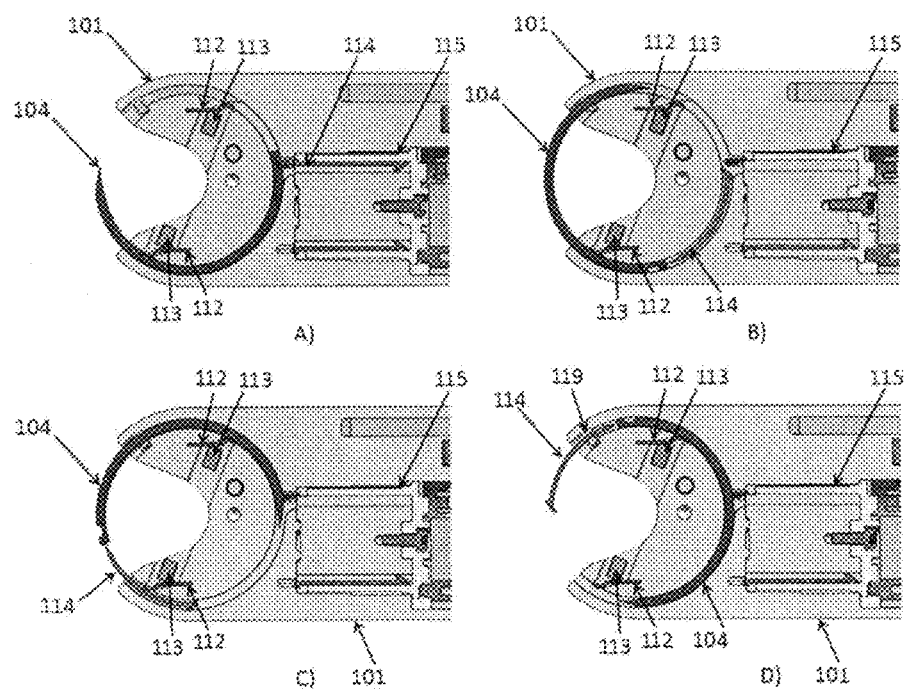
Figure 37: Needle Advancement Sequence
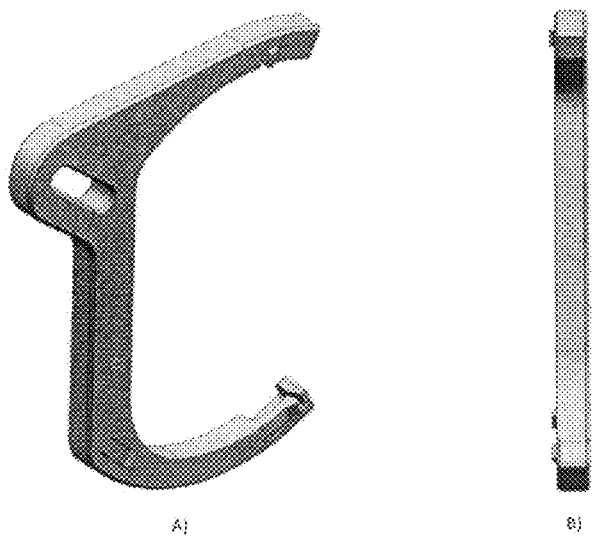
Figure 38: Needle Advancer Arm

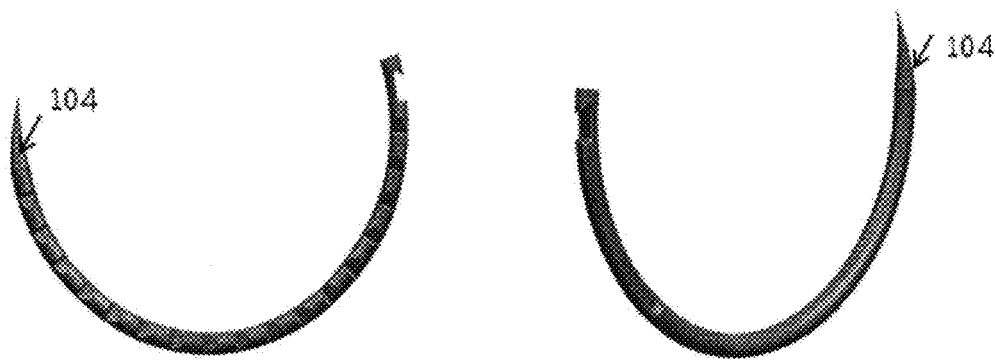
Figure 39: Needle Side View
Figure 40: Needle Isometric View
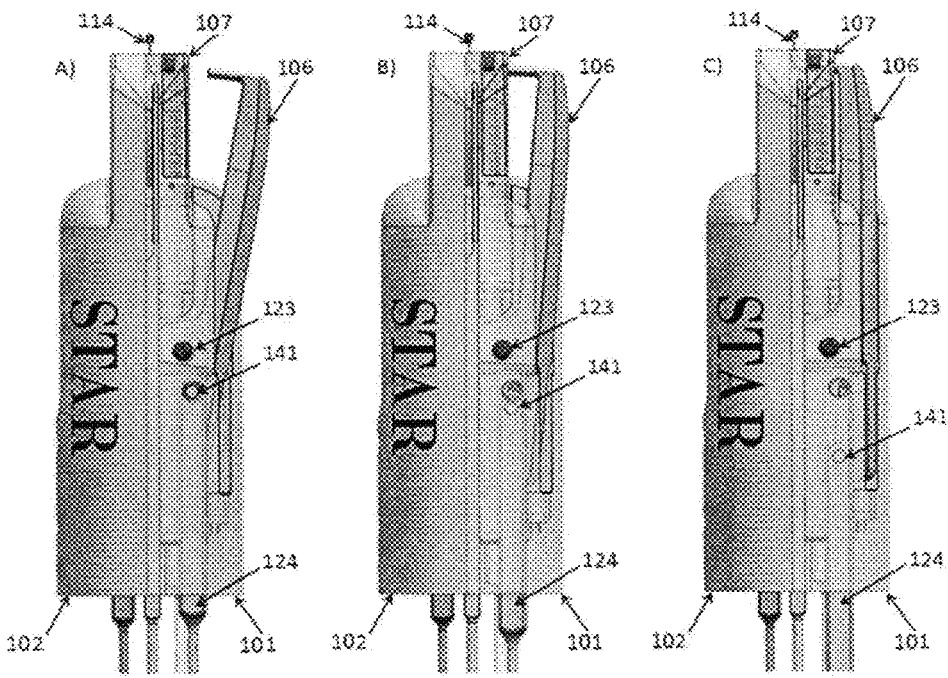
Figure 41: Clasp Closing Actuator

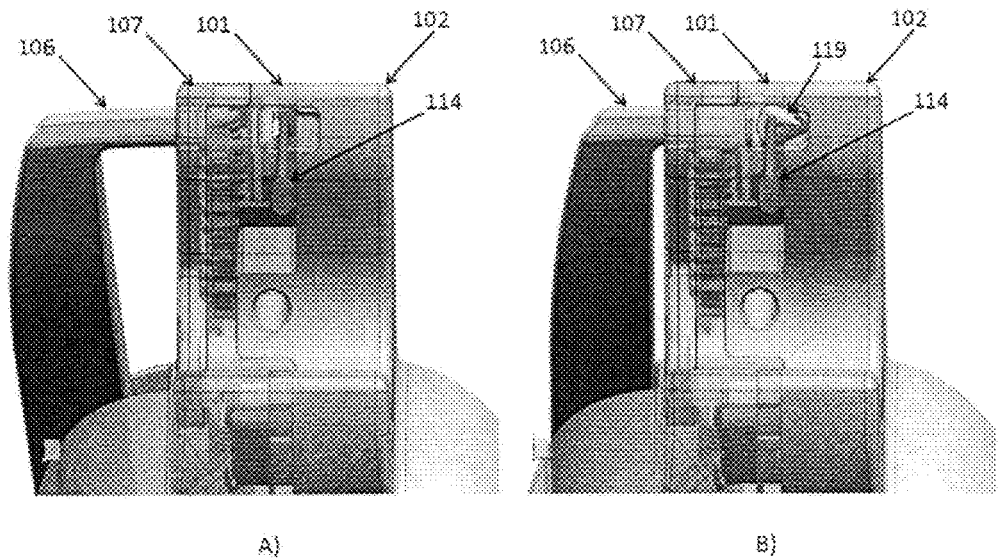
Figure 42: Clasp Closing
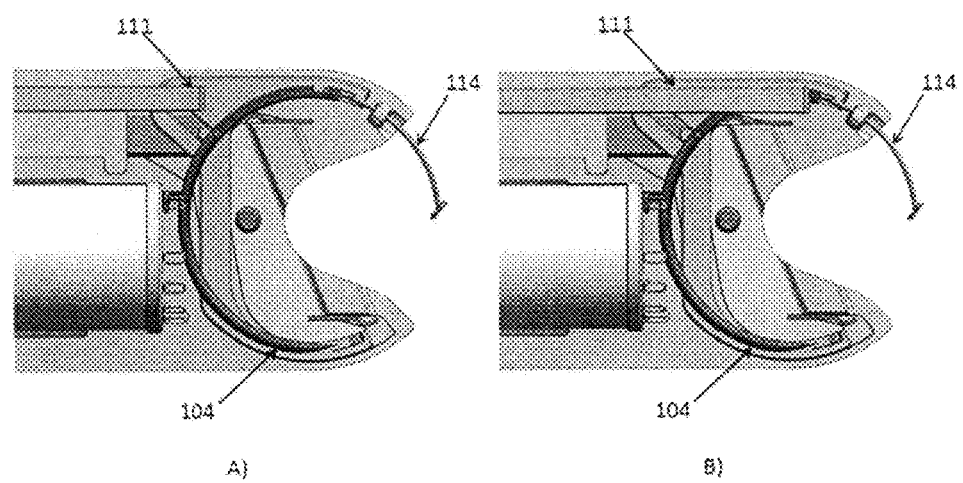
Figure 43: Clip Cutting

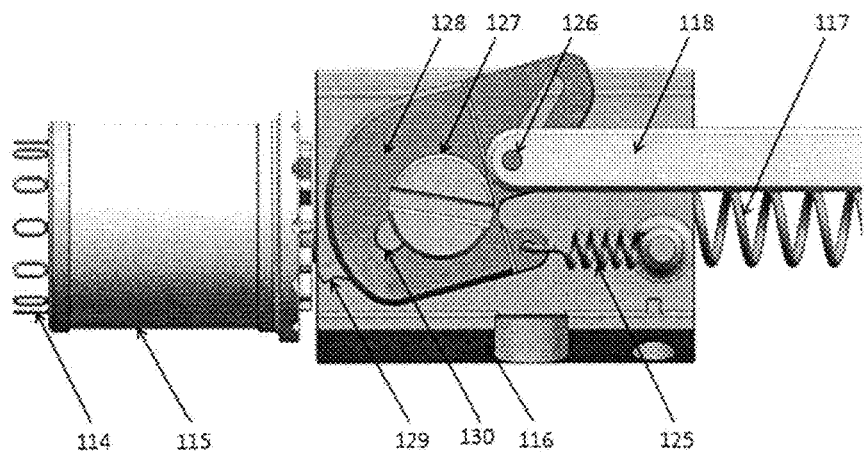
Figure 44: Clip Cartridge Advancement Mechanism (Top View)
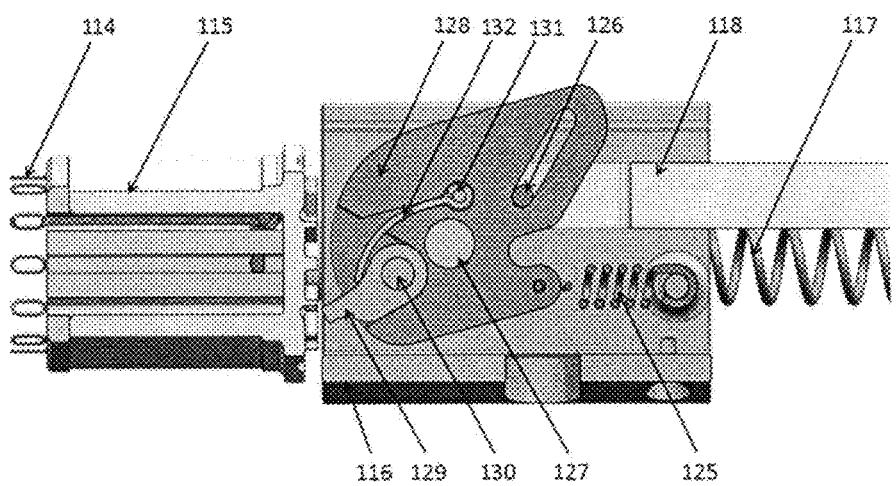
Figure 45: Clip Cartridge Advancement Mechanism (Cross Section Top View)

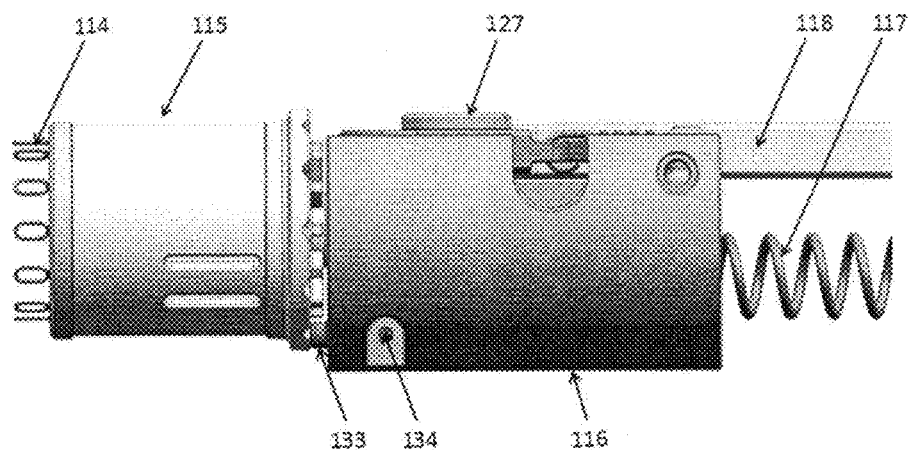
Figure 46: Clip Cartridge Advancement Mechanism (Side View)
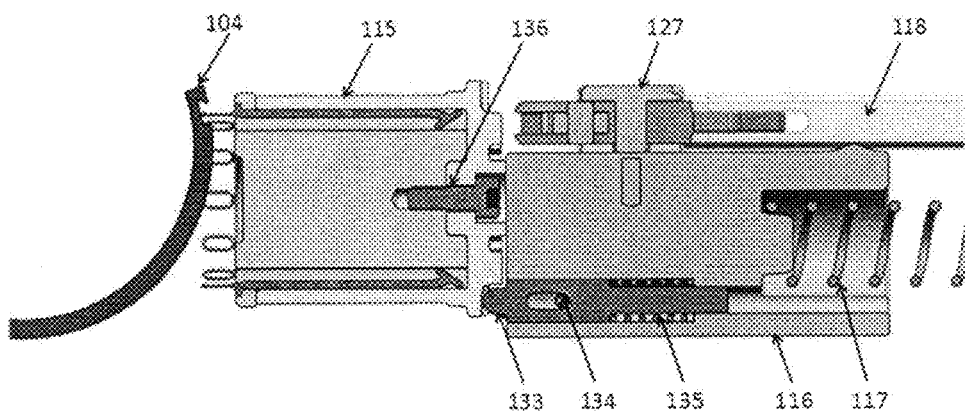
Figure 47: Clip Cartridge Advancement Mechanism (Cross Section Side View)

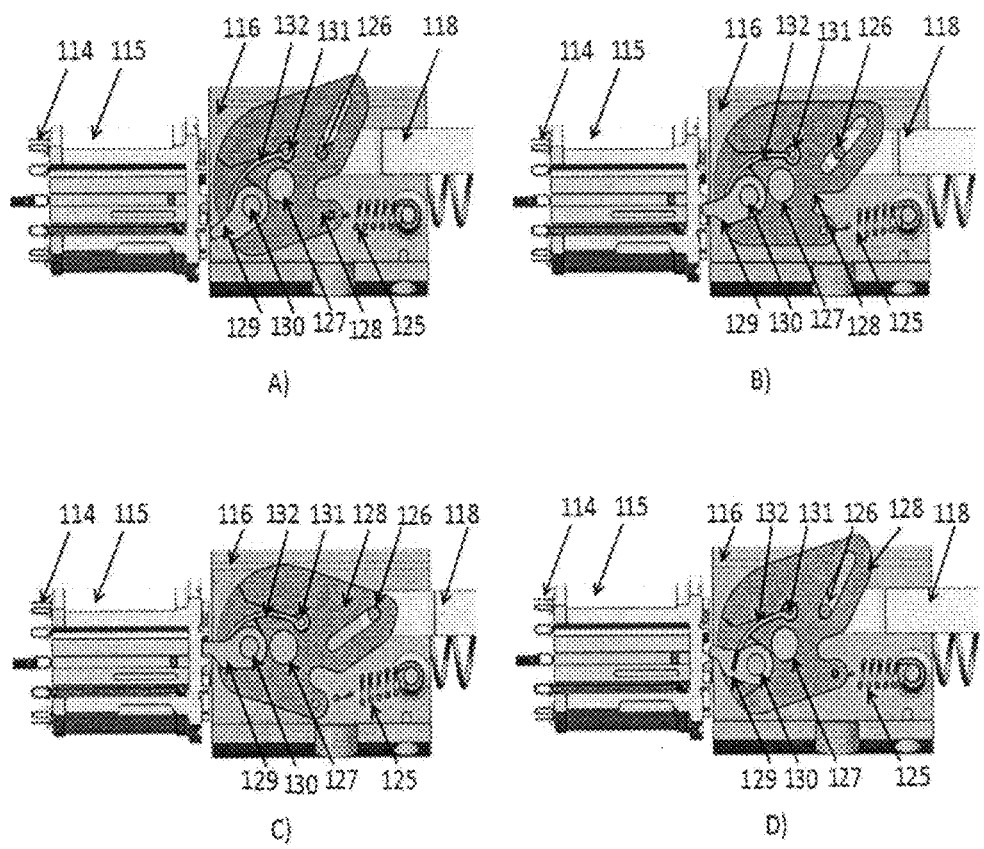
Figure 48: Cartridge Advancement Sequence (Top View)

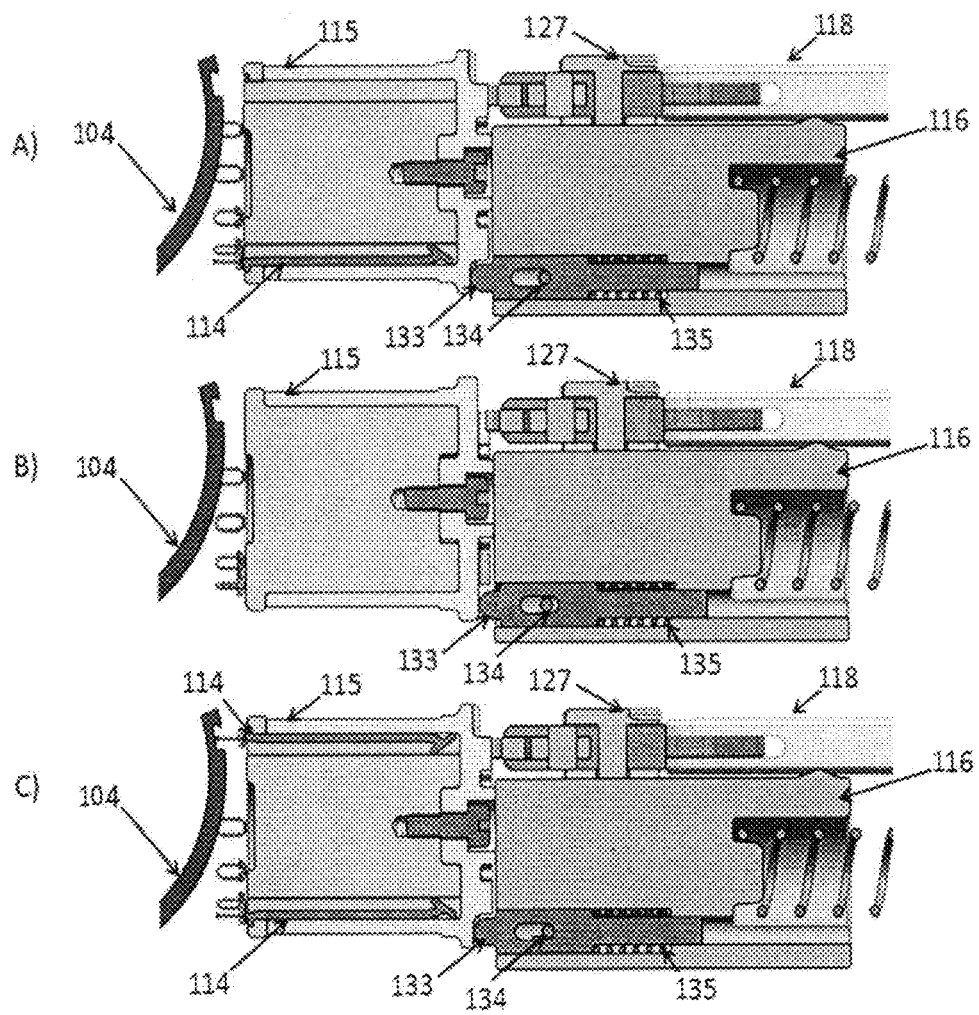
Figure 49: Cartridge Advancement Sequence (Side View)

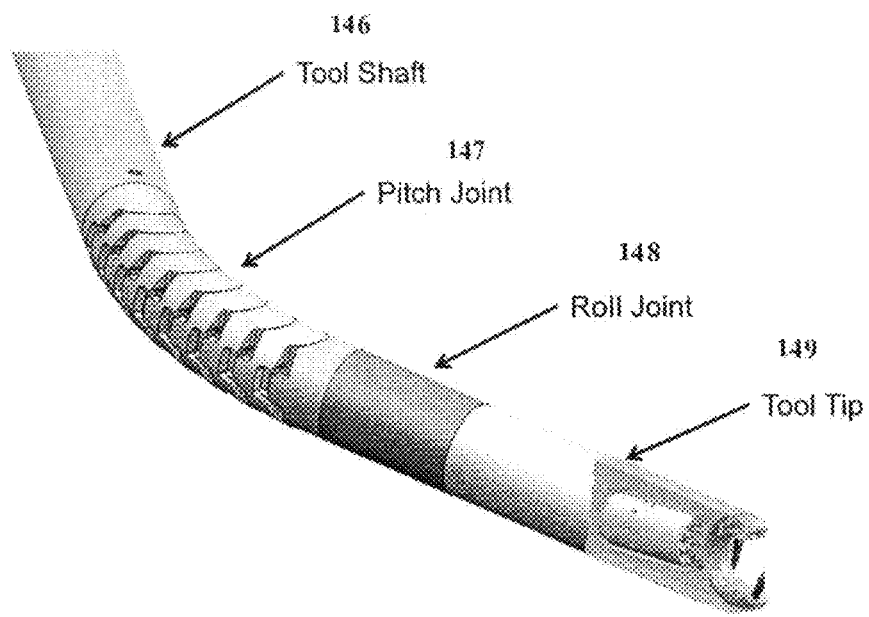
Figure 50: Example of Apparatus Variation with 2 positioning Degrees of Freedom (Pitch and Roll) on Shaft
Figure 51: Operations Flow for the Tool Tip
Step 1: Partially advance needle (pulling attached clip), pierce first lumen
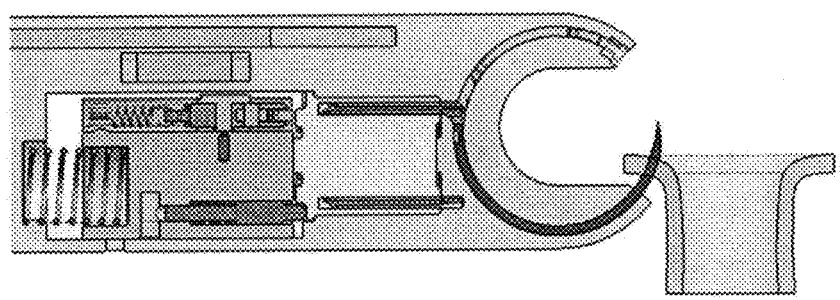

Figure 51: Operations Flow for the Tool Tip (continued)
Step 2: Partially advance needle more, pierce second lumen
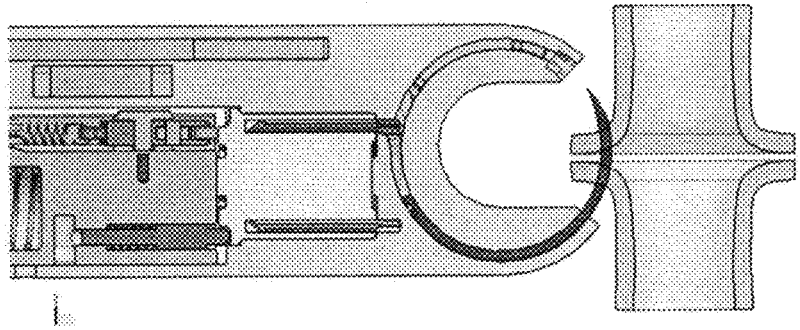
Step 3: Complete needle rotation to pull clip through both lumen
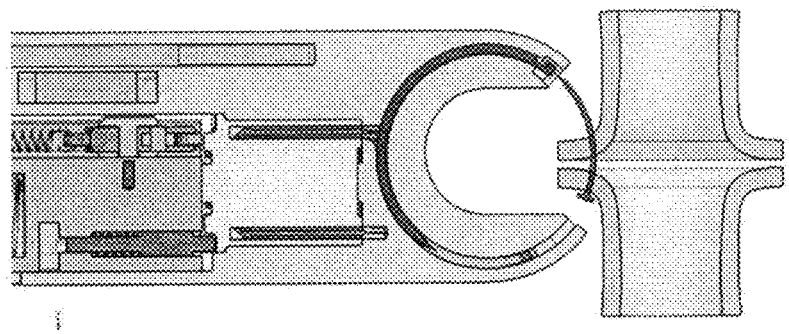
Step 4: Tension clip, deploy clasp, release clip from tool
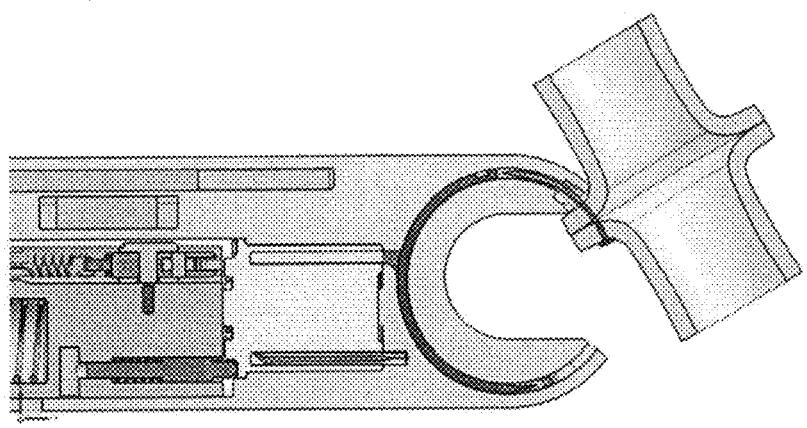

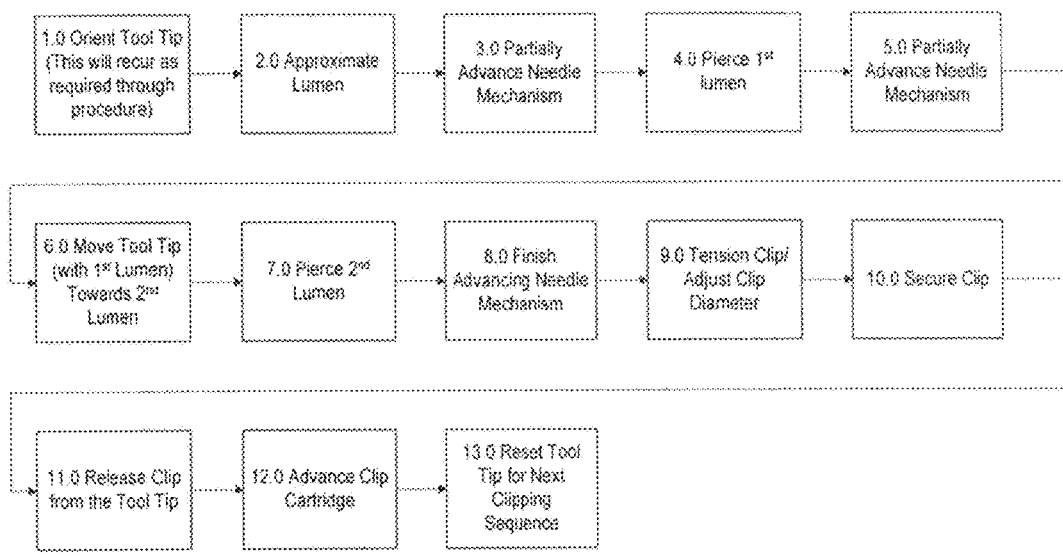
Figure 52: Sequence of Operation for the Clipping Method

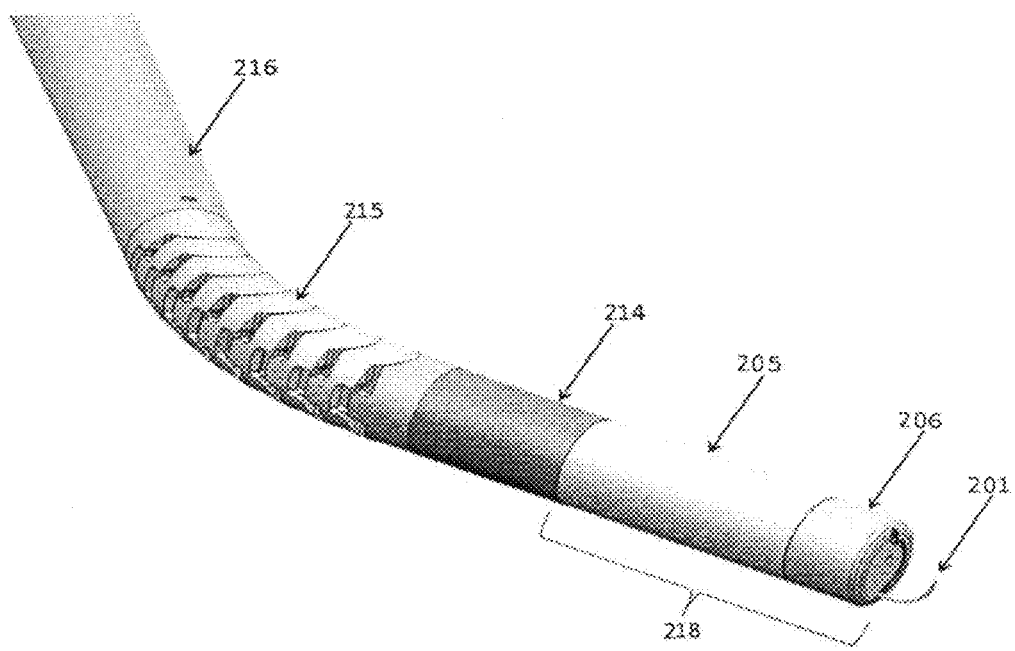
Figure 53 : Tool with Joints
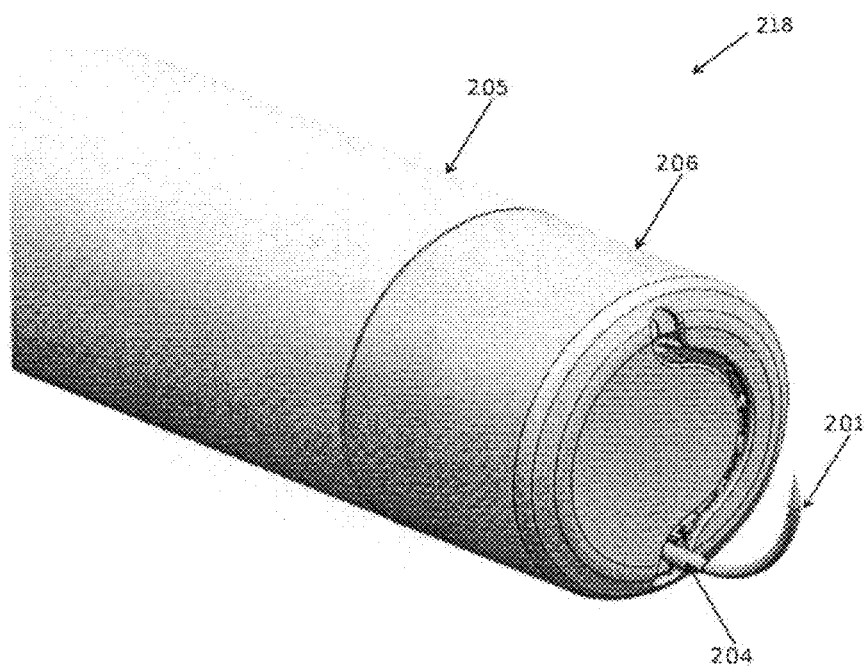
Figure 54 : Shape Memory Alloy Needle Clipping Tool Tip

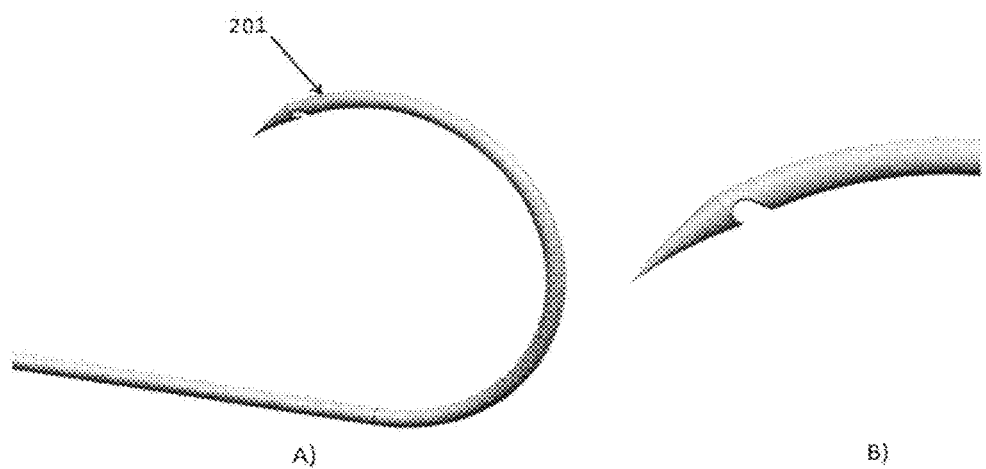
Figure 55: Shape Memory Alloy Needle
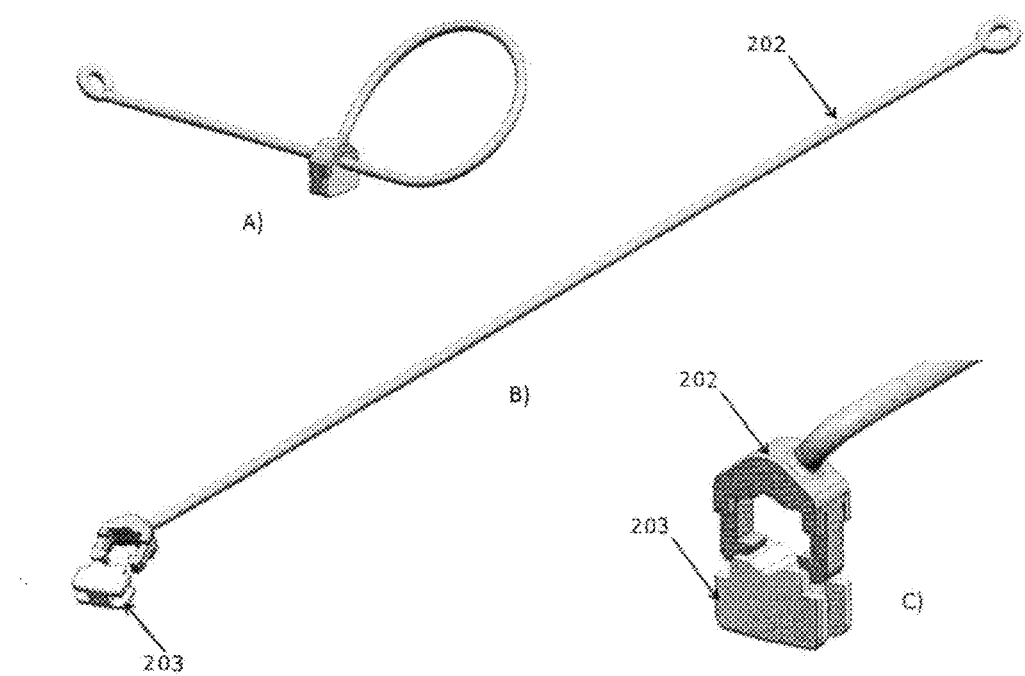
Figure 56: Clip and Clasp

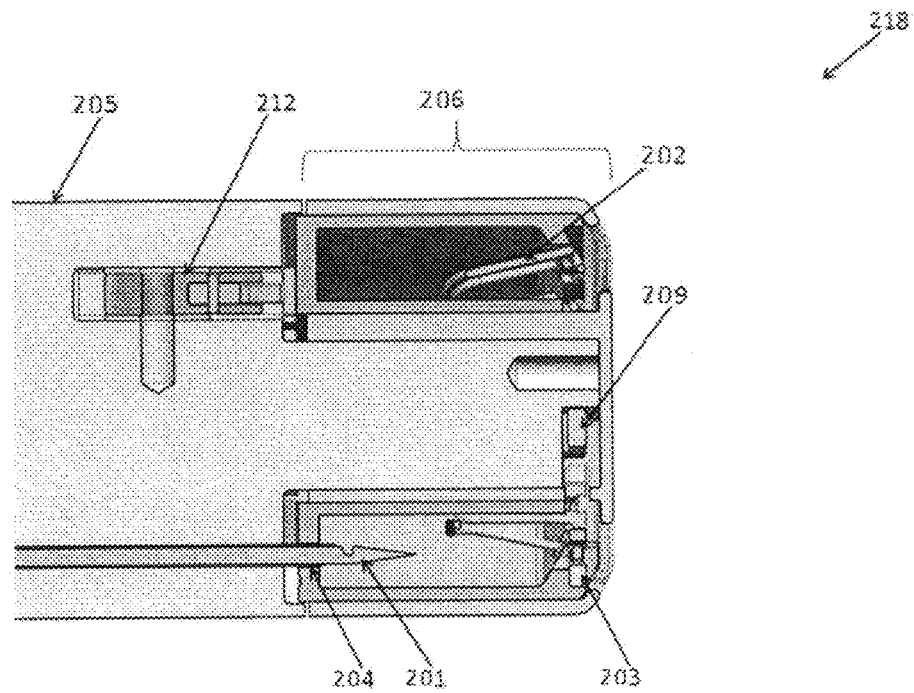
Figure 57A : Sequence 1
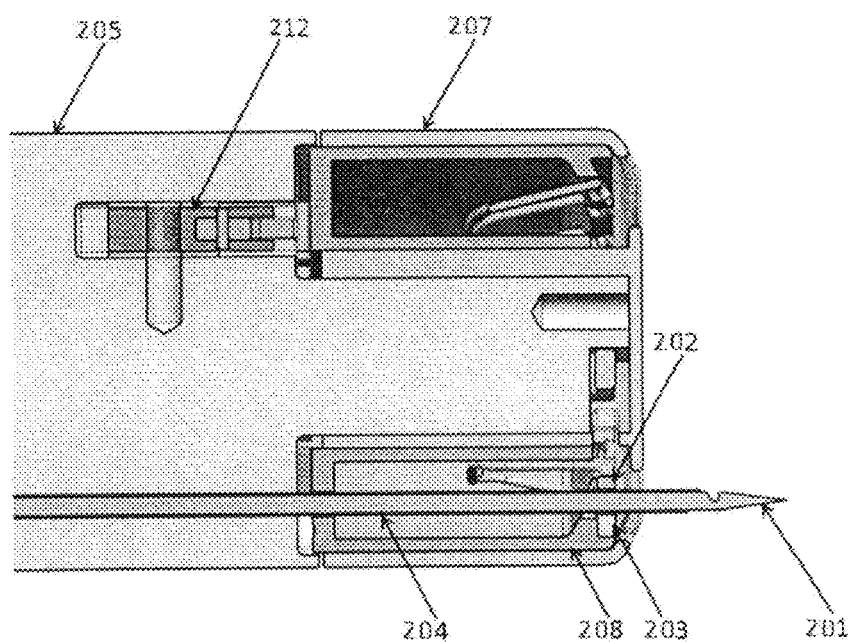
Figure 57B : Sequence 2

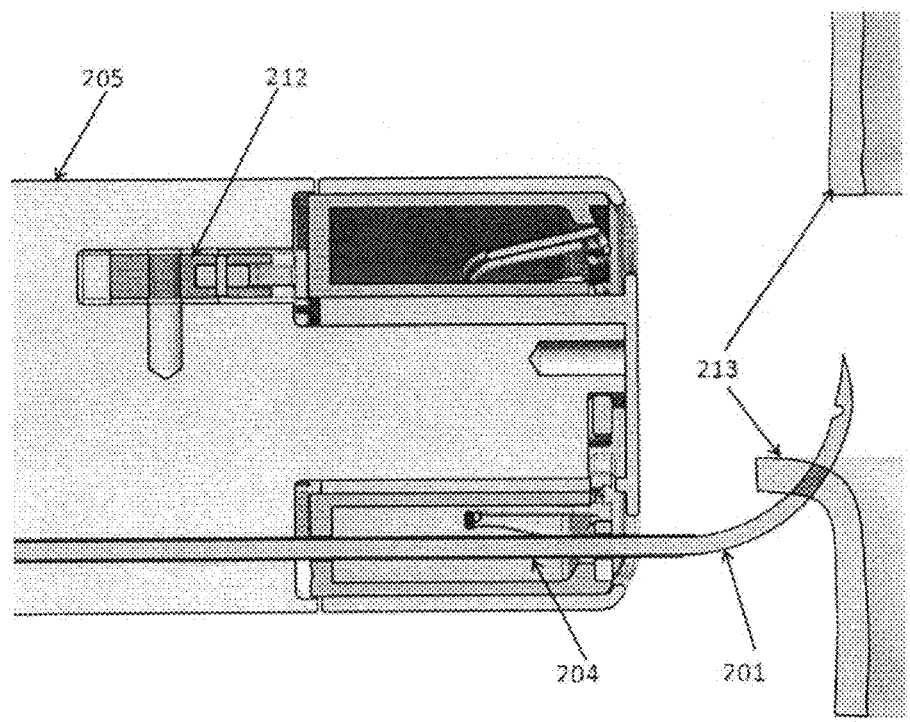
Figure 57C : Sequence 3
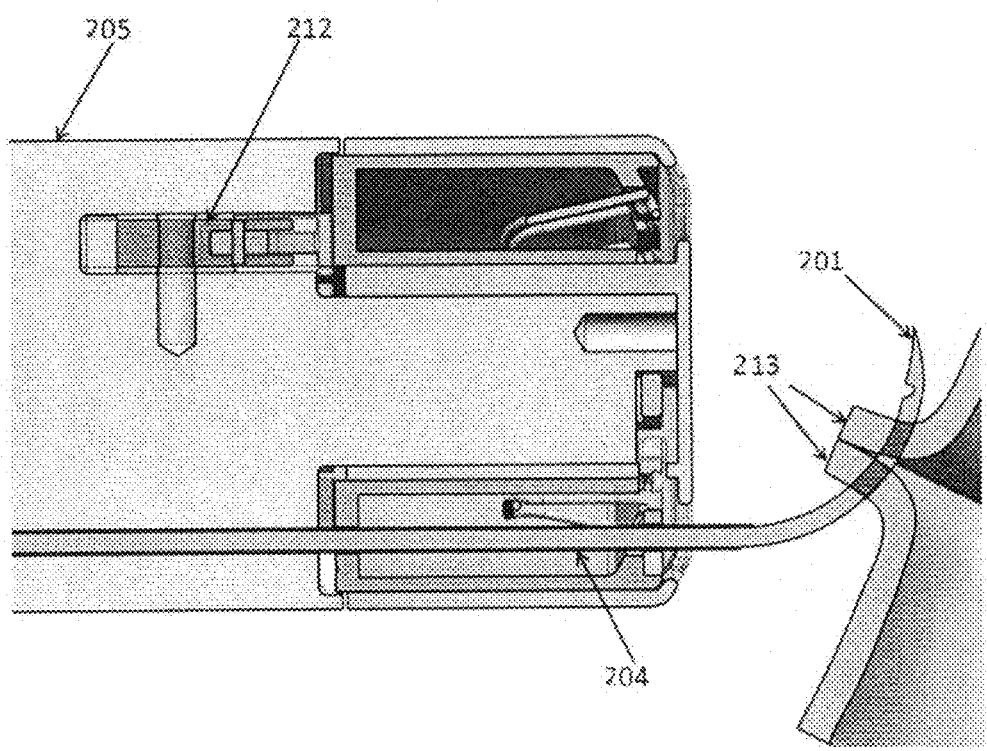
Figure 57D : Sequence 4

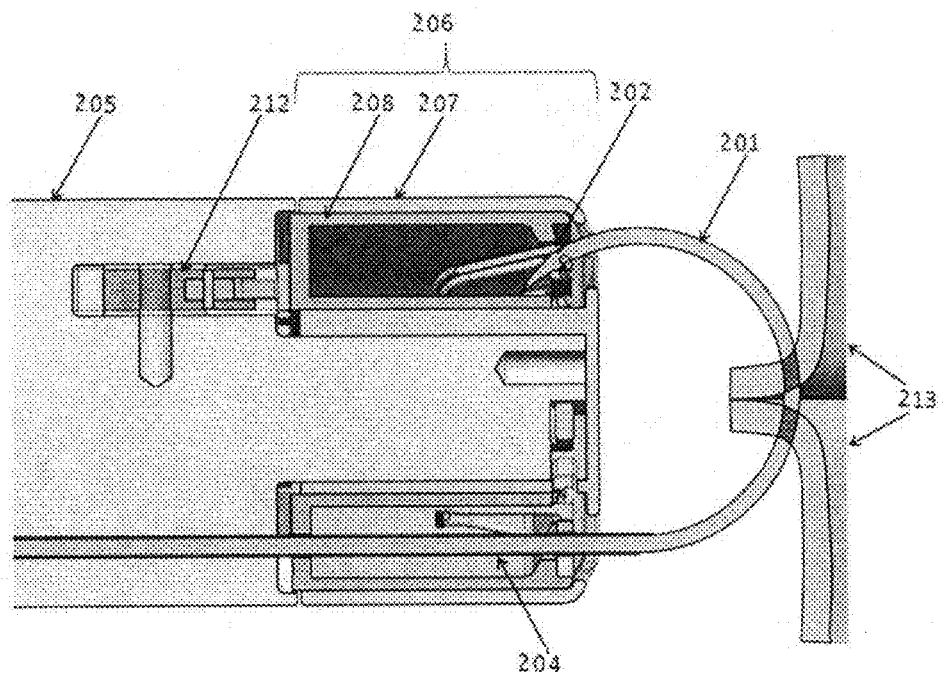
Figure 57E : Sequence 5
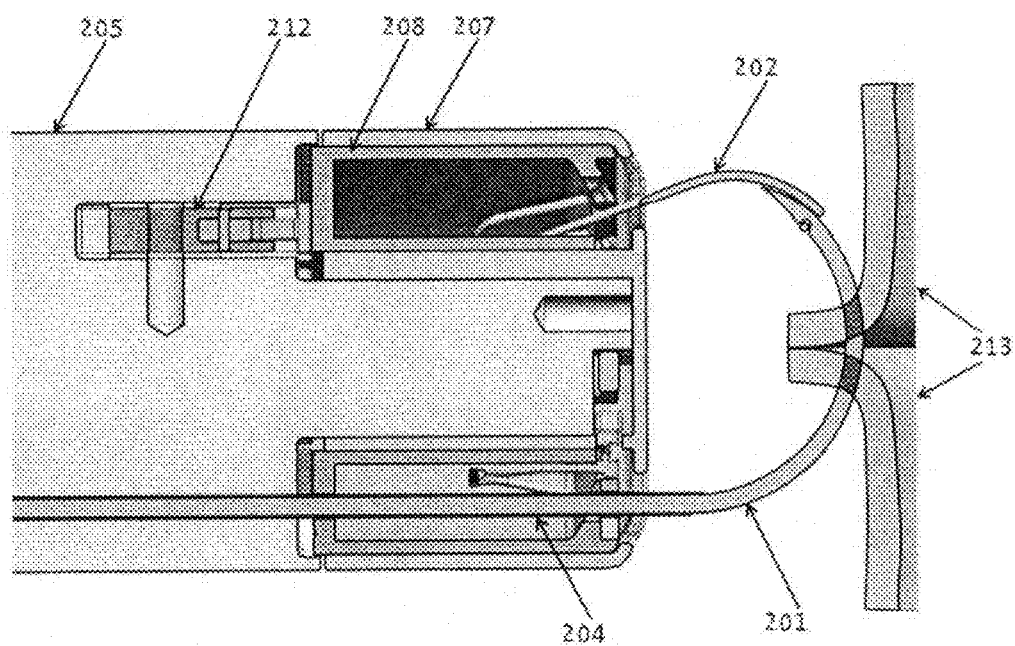
Figure 57F : Sequence 6

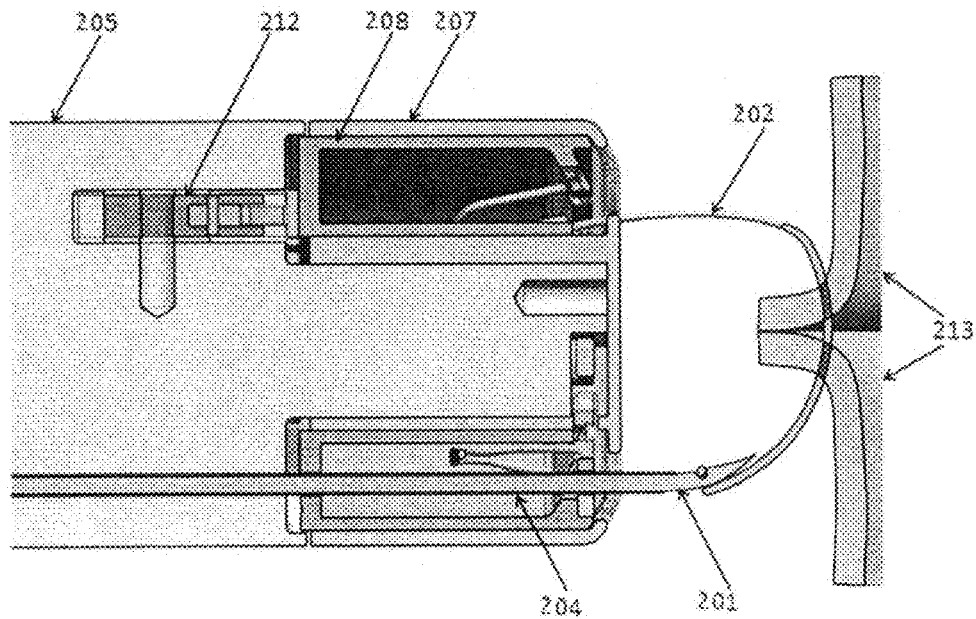
Figure 57G : Sequence 7
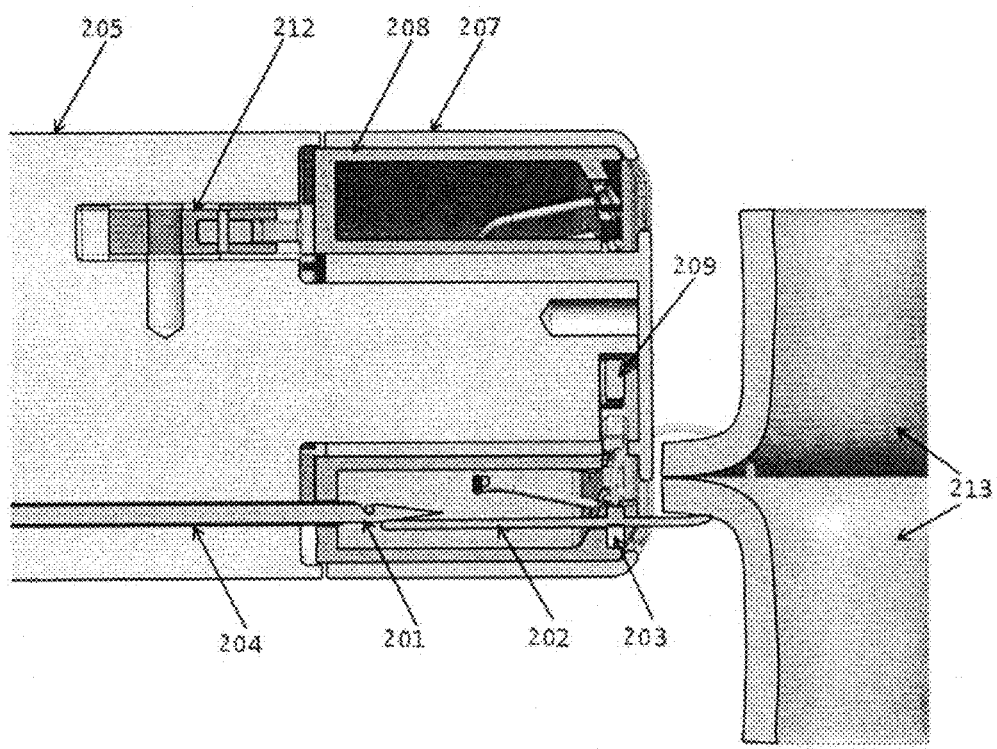
Figure 57H : Sequence 8

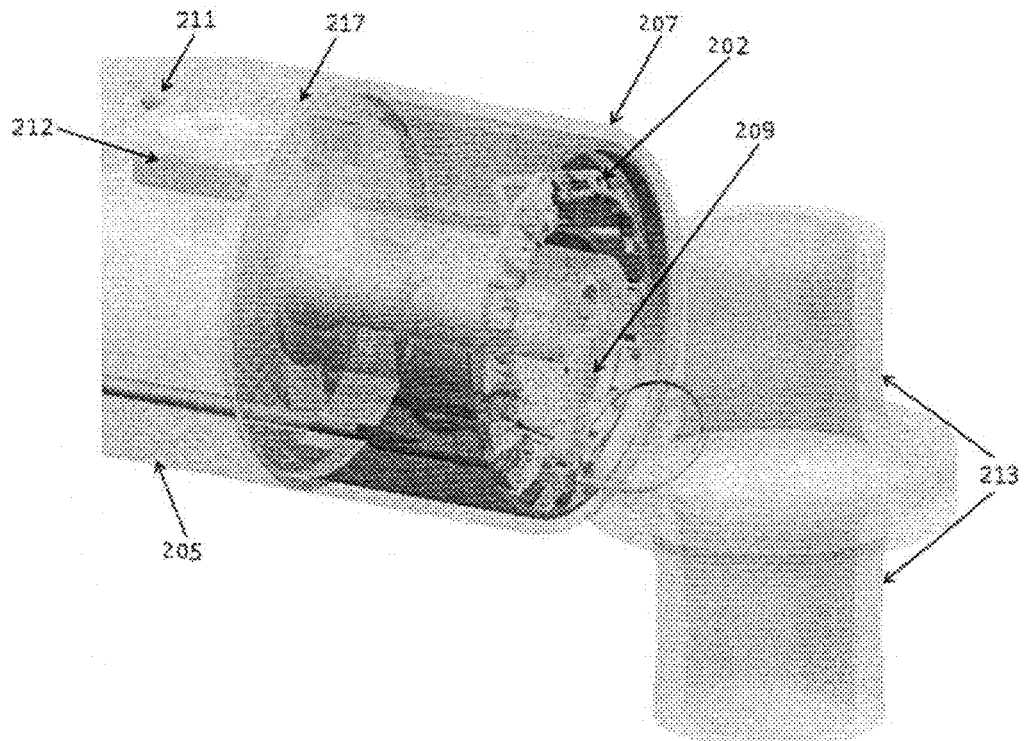
Figure 57I : Sequence 9
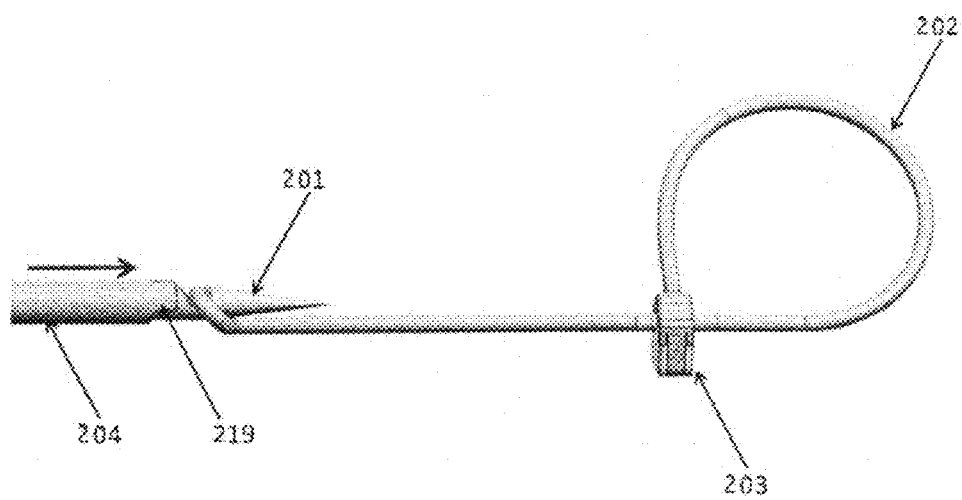
Figure 57J : Sequence 10

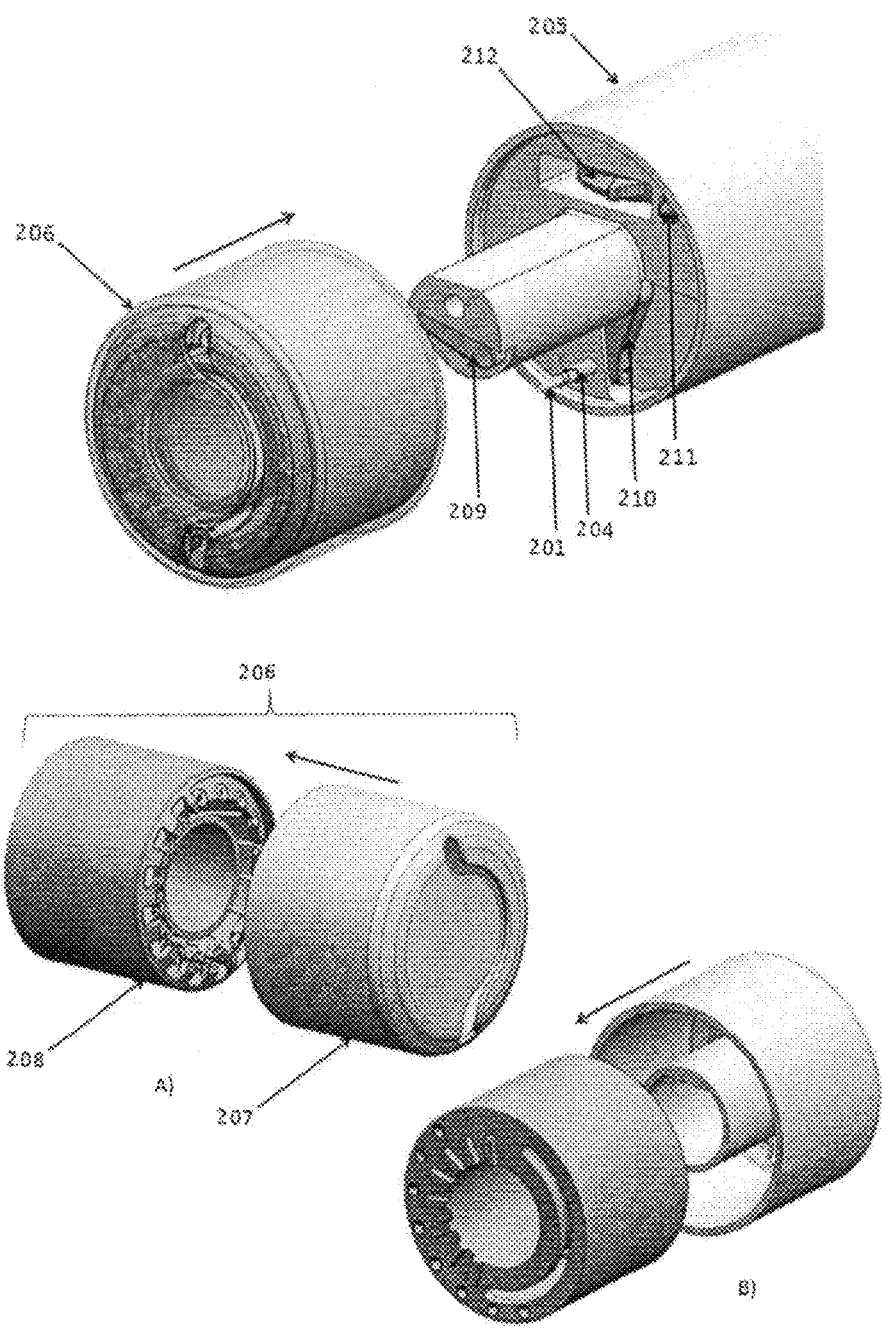
Figure 58 : Clip Cartridge Loading

ANASTOMOSIS CLIPPING TOOL WITH HALF-LOOP CLIP

CROSS REFERENCE TO RELATED APPLICATIONS

This application is based upon and claims the benefit of priority from U.S. Provisional Patent Application No. 61/706,322, filed on Sep. 27, 2012, the entire contents of which are incorporated herein by reference, and from U.S. Provisional Patent Application No. 61/705,875, filed on Sep. 26, 2012, the entire contents of which are incorporated herein by reference.

BACKGROUND

I. Field of the Disclosure

The present invention relates to an apparatus, system, and method for fastening tissue and/or fastening a prosthetic/biologic mesh to tissue. Specifically, it is designed for use in anastomosis surgery (i.e. connecting two tubular structures) to restore continuity after resection, to bypass an unresectable disease process, to close any luminal structure, to provide hemostasis, or to position/secure bioabsorbable or prosthetic mesh for tissue or organ structural weakness. The present invention relates to the process of performing an anastomosis in an end-to-end, side-to-side or an end-to-side fashion as a functional example, but fastening open edges of tissue, securing prosthetic material to tissue, or closure of a bleeding vessel can be accomplished in a similar fashion.

II. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

There are many procedures for pediatric patients that include minimally invasive techniques, but there are few surgeons who are able to perform them due to the challenges they present. Because the patient's anatomy is so small, pediatric surgery faces access and space challenges not found in adult patients. The tiny volume available for tool movement and accommodation when using standard laparoscopic techniques inside the pediatric patient make standard tools unusable; they are simply too large. Once inside the patient, the ability to obtain good camera views is constrained due to limited space availability. This, combined with the reduced size of the anatomy, challenges the surgeon's situational awareness at a time in in the procedure that is especially critical for efficacy.

A common requirement in many surgical procedures is the resection or bypass of a diseased organ. Often the diseased section involves a tubular structure (i.e. artery, bowel, or esophagus) and the resulting ends of the tube must be reattached after performing the resection. This procedure is termed an "anastomosis" and is less difficult to perform in the setting of an open surgery. However, in minimally invasive surgery (MIS) where the procedure is performed through small incisions in the patient's skin, it is extremely difficult to create an anastomosis due to limited space, inadequate camera visualization, and awkward instrument angles. Of all the tasks performed during pediatric minimally invasive surgery, anastomosis creation is probably the most critical to success, and is the portion of the procedure most likely to be impacted by operating constraints. In some cases, it may take as long as two hours to perform. For the surgeon, laparoscopic anastomosis surgery is extremely difficult to learn and perform and is very fatiguing in nature. Increased operating time is also a burden on the healthcare system as it consumes valuable operating room time and adds to overall costs. Most importantly, spending an extended period of time in surgery can negatively impact the patient due to increased anesthesia requirement and additional stress to the body.

U.S. Pat. No. 6,358,258 issued to Arcia et al. discloses an anastomosis device that utilizes multiple flexible needles (designed of nitinol material) that are deployed through multiple curved guide channels. The design utilizes multiple push rods for actuation and is suitable for end-side type anastomosis.

U.S. Pat. No. 7,029,481 issued to Burdulis et al. discloses an anastomosis device that utilizes multiple needles that are simultaneously is pierced through the tissue using a pneumatic cylinder. The needles latch onto small crimps on the opposite end and pull the sutures through the tissue upon retraction. The other end of the device utilizes multiple flexible needles deployed using curved channels and multiple pushrods. The design needs custom needles as the sutures are attached to the distal tip of the needle as opposed to the proximal end found in conventional sutures.

U.S. Patent Application No. 2008/10275472 to Yossepowitch et al. discloses an anastomosis device that utilizes multiple needle deployment through the use of flexible needle and curved guide channels. The design utilizes multiple push rods and requires custom needles to function. Even though the two ends of the design are attached through a flexible coupler, the design lacks a good suture management scheme and will suffer from suture tangling. As described in U.S. Pat. No. 7,029,481, the design requires custom needles as the sutures are attached to the distal tip of the needle as opposed to the proximal end found in conventional sutures.

U.S. Pat. No. 8,123,764 issued to Meade et al. discloses a minimally invasive suturing device that utilizes an actuator that engages a curved suturing needle to cause rotational movement and advance the needle, along with the attached suturing material, through separate segments of tissue thereby forming a stitch. The design provides a good method of creating a stitch, but tying of the suturing material requires a separate discrete process that necessitates input of a laparoscopic grasping tool through a separate port, introducing additional time and uncertainty to the surgical procedure. Furthermore, like conventional method of laparoscopic anastomosis, an additional step of exchanging a grasping tool to a cutting tool is required to remove the suturing material from the needle in order to retrieve the latter.

Aside from the aforementioned patents, various MIS suturing devices are described in the following patents: U.S. Pat. No. 5,954,733 (Yoon) entitled "Suturing Instrument with Rotatably Mounted Needle Driver and Catcher," U.S. Pat. No. 5,665,096 (Yoon) entitled "Needle Driving Apparatus and Methods of Suturing Tissue," U.S. Pat. No. 5,665,109 (Yoon) entitled "Methods and Apparatus for Suturing Tissue," U.S. Pat. No. 5,759,188 (Yoon) entitled "Suturing Instrument with Rotatably Mounted Needle Driver and Catcher," U.S. Pat. No. 5,860,992 (Daniel et al.) entitled "Endoscopic Suturing Devices and Methods," U.S. Pat. No. 6,719,763 (Chung) entitled "Endoscopic Suturing Device," and U.S. Pat. No. 6,755,843 (Chung) "Endoscopic Suturing Device," U.S. Pat. No. 8,100,922 entitled "Curved Needle Suturing Tool" (Ethicon Endo-Surgery), U.S. Pat. No. 6,425, 887 entitled "Multidirectional Needle Medical Device" (Cook Incorporated), U.S. Patent Application No. 2003/0032929 entitled "Hollow Curved Superelastic Medical Needle and Method" (Rex Medical); and U.S. Patent Application No. 2008/0097391 entitled "Articulating Laparoscopic Device and Method for Delivery of Medical Fluid" (Rex Medical).

SUMMARY

While the above patents propose methods of achieving more efficient MIS suturing, none address the difficulty with subsequent knot tying. Thus, there is a need for a fully automated/assisted laparoscopic anastomosis device that can reduce procedure time and operating costs. The device will also be of interest to surgeons as it would minimize dependence on a surgeon's dexterity and experience for producing an efficacious anastomosis.

To our knowledge, there are currently no devices or patents that deliver a flexible fastener, such as a clip, or a staple, or a T-suture that behaves like suture but can be closed with a simple holder, such as a clasp, a stopper, or a clamp. While there is a commercial product that can be used on suture to replace knots (LAPRA-TY®), the present invention combines the functions of tissue piercing and fastening, joining lumen together, and securing a holder, which obviates the need to employ multiple tools to perform this complex portion of an anastomosis procedure. Use of a holder that is a half-loop clip is also novel.

Laparoscopic anastomosis surgery involves complicated, technically-demanding movements, and often requires the surgeon to tie knots in single-suture stitches and make frequent instrument changes during the procedure. A fastening device is intended to provide surgeons a way to more easily and efficiently join two lumen by placing intermittent fasteners, rather than sutures that require complicated knot-tying and instrument changes, to achieve the same closures. The present surgical device has the potential to provide the means for increasing procedure efficiency and decreasing operating times, and is consistent with our goal to make pediatric surgery more precise, less invasive, and safer.

The anastomosis segment of a minimally invasive procedure for pediatric patients requires intense concentration and dexterity, and often takes more than an hour to perform. Because it most often occurs near the end of a procedure, surgeon fatigue plays a role in the efficacy of the anastomosis. The present surgical device provides the surgeon assistance with this complex manual task by reducing the frequency of instrument changes, and eliminating the need to place multiple serial sutures that require difficult knot tying and cutting suture.

A goal of the fastening device disclosed herein is to minimize a number of necessary trocars in order to reduce patient pain. Another goal of the present invention is to reduce suturing time and frequency of instrument changes in order to increase procedure efficiency and reduce surgeon fatigue.

These objectives, among others, are attained by the present invention described in this disclosure.

In an aspect of the disclosure, a tool to fasten tissue portions or to fasten a prosthetic element to tissue, includes a gripper to hold one or more portions of tissue, a needle, an actuator to drive the needle, a fastener cartridge to store one or more tissue fasteners, a holder cartridge to store one or more holders, and a holder applier to secure one of the holders on one of the fasteners. The actuator drives the needle so that the needle pulls a first fastener of the one or more tissue fasteners from the fastener cartridge. The actuator drives the needle through the one or more portions of tissue held by the gripper to form a hole in the one or more portions of tissue. The needle pulls a leading portion of the first fastener through the hole without a trailing portion of the first fastener being pulled through the hole. The holder applier secures a first holder of the one or more holders from the holder cartridge onto the leading portion of the first fastener.

In an aspect of the disclosure, the tool further includes a cutter to cut one of the fasteners, and the cutter cuts off a front end of the leading portion of the first fastener that protrudes from the first holder that is secured onto the first fastener.

In an aspect of the disclosure, the needle is a curved needle.

In an aspect of the disclosure, the one or more fasteners include at least one of a clip, a staple, and a T-suture.

In an aspect of the disclosure, the one or more holders include at least one of a clasp, a stopper, and a clamp.

In an aspect of the disclosure, the needle includes a piercing end and an opposing end that includes a hook to pull a loop at a front end of the leading portion of the first fastener.

In an aspect of the disclosure, the one or more fasteners and the one or more holders are made of at least one of a polymer material, a bioabsorbable material, and a biocompatible material.

In an aspect of the disclosure, the actuator drives the needle around a 360° advancement path.

In an aspect of the disclosure, the gripper includes two arms, and at least one of the two arms is a curved arm that is movable.

In an aspect of the disclosure, the tool further includes a fastener advancing mechanism to advance a second fastener to a ready position to be pulled by the needle after the first fastener is pulled from the fastener cartridge.

In an aspect of the disclosure, the tool further includes a holder advancing mechanism to advance a second holder to a ready position to be applied by the holder applier after the first holder is removed from the holder cartridge by the holder applier.

In an aspect of the disclosure, the tool further includes a tool tip body, a shaft, and a mechanism. The tool tip body includes the gripper, the needle, the actuator, the fastener cartridge, the holder cartridge, and the holder applier. The mechanism joins the tool tip body to the shaft, and the mechanism allows the tool tip body to be movable with at least two degrees of freedom.

In a further aspect of the disclosure, a manual handheld device to fasten tissue portions or to fasten a prosthetic element to tissue includes the tool.

In another aspect of the disclosure, a system to perform a surgical procedure includes the tool. The system further includes a positioning device to position the tool at a tissue fastening location, a sensor to track a desired tissue fastening point, a fastening location specification unit to select one or more tissue fastening points, an illumination device to illuminate the fastening location, and a controller to control operation of the tool and the positioning device.

An additional aspect of the disclosure includes a method to fasten tissue. The method includes orienting a tool to a configuration to begin a sequence of fastening the tissue. The method includes gripping a first piece of the tissue to be fastened with a gripper of the tool. The method includes advancing a needle of the tool to pierce a first piece of the tissue to be fastened. The method includes opening the gripper while the needle remains pierced through the first piece of the tissue to be fastened. The method includes gripping a second piece of the tissue to be fastened with the gripper. The method includes further advancing the needle to pierce the second piece of the tissue to be fastened. The method includes advancing the needle to pull a leading portion of a fastener stored in the tool through pierced holes in the first and second pieces of the tissue without a trailing portion of the fastener being pulled through the pierced holes. The method also includes securing a holder stored in the tool onto the leading portion of the fastener with a holder applier of the tool.

In an aspect of the disclosure, the method further includes tensioning the fastener by advancing the needle to pull the fastener before securing the holder.

In an aspect of the disclosure, the method further includes cutting a front end of the leading portion of the fastener that protrudes from the holder that is secured onto the fastener.

The foregoing paragraphs have been provided by way of general introduction, and are not intended to limit the scope of the following claims. The described embodiments, together with precise advantages, will be best understood by reference to the following detailed description taken in conjunction with the accompanying drawings.

BRIEF DESCRIPTION OF THE DRAWINGS

A more complete appreciation of the disclosure and the attendant advantages thereof will be better understood by reference to the accompanying drawings and the subsequent detailed description, where:

FIG. 1 shows an isometric view #1 of a tool tip according to a first embodiment of the invention.

FIG. 2 shows another isometric view #2 of the tool tip.

FIG. 3 shows side view #1 of the tool tip.

FIG. 4 shows side view #2 of the tool tip.

FIG. 5 shows illustrations of a clasp, a clip, and how these components interact when engaged.

FIG. 6 shows an illustration of loading the clip cartridge.

FIG. 7 shows cross-sectional view #1 of the tool tip.

FIG. 8 shows a detail view of a clasp cartridge.

FIG. 9 shows cross-sectional view #2 of the tool tip.

FIG. 10 shows a needle advancer arm actuation system.

FIG. 11 shows a needle advancement sequence.

FIG. 12 shows a detail view of a needle advancer arm.

FIG. 13 shows a side view of a needle.

FIG. 14 shows an isometric view of the needle.

FIG. 15 shows an illustration of a clasp closing actuator.

FIG. 16 shows an illustration of a clasp closing mechanism.

FIG. 17 shows an illustration of clip cutting.

FIG. 18 shows a top view of a clip cartridge advancement mechanism.

FIG. 19 shows a variation of a clipping apparatus with 2 positioning degrees of freedom (pitch and roll) on a shaft.

FIG. 20 shows an illustration of an operations flow of a mechanical actuation system.

FIG. 21 shows a flow chart of a sequence of operation for an anastomosis clipping method.

FIG. 22 shows an illustration of a half-loop clip and clasp as seen after deployment in tissue.

FIG. 23 shows an illustration of a robotic variation of the clipping system.

FIG. 24 shows a systems block diagram depicting system architectural blocks and a workstation/robotic workcell of a shared image-guided anastomosis system.

FIG. 25 shows an example of the robot-driven variation of the clipping apparatus.

FIG. 26 shows an illustration of a manual/handheld variation of the clipping apparatus.

FIG. 27 shows isometric view #1 of a tool tip according to a second embodiment of the invention.

FIG. 28 shows another isometric view #2 of the tool tip.

FIG. 29 shows side view #1 of the tool tip.

FIG. 30 shows side view #2 of the tool tip.

FIG. 31 shows an illustration of a clasp, a clip, and how these components interact when engaged.

FIG. 32 shows an illustration of loading a clip cartridge.

FIG. 33 shows cross-sectional view #1 of the tool tip.

FIG. 34 shows a detail view of a clasp cartridge.

FIG. 35 shows cross-sectional view #2 of the tool tip.

FIG. 36 shows a needle advancer arm actuation system.

FIG. 37 shows a needle advancement sequence.

FIG. 38 shows a detail view of a needle advancer arm.

FIG. 39 shows a side view of a needle.

FIG. 40 shows an isometric view of the needle.

FIG. 41 shows an illustration of a clasp closing actuator.

FIG. 42 shows an illustration of a clasp closing mechanism.

FIG. 43 shows an illustration of clip cutting.

FIG. 44 shows a top view of a clip cartridge advancement mechanism.

FIG. 45 shows a cross-section top view of the clip cartridge advancement mechanism.

FIG. 46 shows a side view of the clip cartridge advancement mechanism.

FIG. 47 shows a cross-sectional side view of the clip cartridge advancement mechanism.

FIG. 48 shows a top view of a cartridge advancement sequence.

FIG. 49 shows a side view of the cartridge advancement sequence.

FIG. 50 shows a variation of a clipping apparatus with 2 positioning degrees of freedom (pitch and roll) on a shaft.

FIG. 51 shows an illustration of an operations flow of a mechanical actuation system.

FIG. 52 shows a flow chart of a sequence of operation for a clipping method.

FIG. 53 a clipping apparatus according to a third embodiment of the invention with 2 positioning degrees of freedom (pitch and roll) on a shaft.

FIG. 54 shows an illustration of a shape memory alloy needle clipping tool tip.

FIG. 55 shows an illustration of a shape memory alloy needle.

FIG. 56 shows an illustration of a clasp, a clip, and how these components interact when engaged.

FIGS. 57A to 57J show sequence of operations within a tool tip mechanical actuation system.

FIG. 58 shows loading of a clip cartridge.

DETAILED DESCRIPTION OF THE ILLUSTRATIVE EMBODIMENTS

Referring to the drawings, like reference numerals designate identical or corresponding parts throughout the several views.

The figures are not to scale, and some features may be exaggerated or minimized to show details of particular elements, while related elements may have been eliminated to prevent obscuring novel aspects. Therefore, specific structural and functional details disclosed herein are not to be interpreted as limiting, but merely as a basis for the claims, and as a representative basis for teaching one of ordinary skill in the art to variously employ the present invention.

The illustrative embodiments described herein are directed to a surgical apparatus, system, and method for fastening tissue. As required, embodiments of the present invention are disclosed herein. However, the disclosed embodiments are merely exemplary, and it should be understood that the invention may be embodied in many various and alternative forms.

The tool described herein has been conceived to quickly deploy a fastener to oppose two pieces of tissue for the purposes of relieving a surgeon of the challenging task of tying interrupted sutures during a laparoscopic procedure. The illustrative embodiments of this tool can also be extended for use during open procedures and should not be limited to laparoscopic procedures. Furthermore, this tool should not be limited to only fastening tissues and should be considered for use in any procedure where two articles are to be fastened together through the deployment of discrete fasteners from a loadable cartridge. The tool tip is intended to be positioned and actuated through the means of an automated, master-slave, or teleoperated robotic system, or in the form of a manual tool manipulated and actuated by a user.

The focus of the following description of the tool is chosen to be in a medical environment as an example. In the medical environment, this device is intended to be used to replace the task of traditional suturing for wound closure or other medical procedures requiring the opposition of two tissues, i.e. anastomosis. The device delivers discrete fasteners through the tissues being opposed by performing the following basic functions:

1. Capture a first portion of a targeted anatomy.
2. Capture a second portion of the targeted anatomy.
3. Deploy a fastener through both portions of the targeted anatomy and tension the fastener in order to optimize healing of the interface.
4. Apply a holder to the deployed fastener in order to secure the fastener at a desired tension/closure length.
5. Release the repaired interface (anatomy, fastener, and holder) from the tool.

The clipping device described herein is of particular use for laparoscopic anastomosis in both pediatric and adult patients. However, it may also be used in lieu of general laparoscopic suturing (both continuous and interrupted).

The tool also contains a cartridge of fasteners and a cartridge of holders that can be cycled during the medical procedure, to allow deployment of numerous fasteners in quick succession. At the end of the medical procedure or if additional fasteners are required once the cartridge is emptied, the cartridges can be removed from the tool and replaced, minimizing any down time during a procedure for reloading.

I. First Illustrative Embodiment

In a first illustrative embodiment, FIG. 1 through FIG. 4 show exterior views of a tool tip to highlight a general profile. The circular profile of the tool allows the tool to fit through a cannula port used during laparoscopic surgeries, while a tapered opening at the tip of the tool provides increased access to tissues. The tool tip includes two halves, a tool body right 1 and a tool body left 2, which encapsulate the internal mechanisms and are held together by a tool body screw 5. It should be noted that the tool is split for assembly reasons and could be secured together via other methods such as clips or tabs instead of the tool body screw 5. Moreover, it is also feasible to construct the tool tip with a uni-body construction.

The tool has been designed to deliver discrete clips through tissue and apply a clasp to secure the tissue together. The clip and clasp are shown in FIG. 5. The clip 10 is a flexible suture-like shape that consists of a loop on one end to hook onto a needle 3, and a flat wider tab at the other end that stops the clip 10 from being pulled completely through the tissue. The clasp 11 is a flexible piece of polymer that has a latch molded into it such that when it is flexed over the clip 10, the latch engages and secures the clasp 11 around the clip 10, as shown in FIG. 5. The clip 10 and clasp 11 are made from a molded polymer that is biocompatible, and possibly also bioabsorbable, for surgical applications, but could also be made from a variety of other materials such as nylon or polypropylene depending on the intended use of the tool. The clip 10 and clasp 11 have been designed such that they are each loaded into reloadable cartridges which can then be loaded into the tool.

FIG. 6 shows a reloadable clip cartridge 12 which consists of a predetermined number of clips 10 housed in a clip cartridge housing. The loaded clip cartridge 12 can then be loaded into the tool.

Referring to FIG. 2 and FIG. 7, loading of the clip cartridge 12 into the tool is accomplished by first removing a cartridge cap 9 from the tool body right 1 in the illustrative example. This provides access to the clip cartridge 12 as well as a clip cartridge advance mechanism 13 to advance a position of the clips 10 housed in the clip cartridge 12. The clip cartridge 12 can be installed and removed through a port that was covered by the cartridge cap 9. Once the clip cartridge 12 is reloaded with clips, it is re-installed into the tool.

FIG. 8 provides a detailed view of a clasp cartridge 8. The clasp cartridge 8 includes a cover that houses a predetermined number of clasps 11 being contained by a clasp retaining tab 35. The clasp cartridge 8 is loaded onto the tool body right 1. FIG. 4 shows a clasp pusher spring 34 that pushes the clasps 11 such that when the clasp retaining tab 35 is removed, the clasps 11 are pushed forward into a forward deployment position.

There are five main mechanisms contained within the tool tip that provide the functionality to deliver a clip and to perform the basic functions. These are:

1. A gripper;
2. A needle advancer;
3. A clasp applier;
4. A clip cutter; and
5. A clip cartridge advancer.

A gripper is detailed in FIG. 1, and includes forceps or gripper arms 7, at least one arm of which is movable. A gripper drive pulley 24 that is shown in FIG. 9, for example, is used to drive a movable arm of the forceps or gripper arms 7. Any other mechanism, however, may be used to activate an opening and closing motion of the gripper. The gripper thus enables the tool tip to capture a target portion of tissue securely between the forceps or gripper arms 7. With the target portion of tissue secured by the gripper, this tissue can be easily pierced by the needle 3 without the tissue simply being pushed out of the way by the needle 3. A gripper assembly cover 4 covers at least a portion of the gripper, and the assembly cover 4 is secured to the tool body left 2 by a gripper assembly cover screw 6.

A needle advancer mechanism is detailed in FIG. 9, FIG. 10, and FIG. 11. The needle advancer mechanism is used to position the clipping tool needle 3 such that both halves of the target anatomy may be captured. The needle advancer mechanism is then subsequently used to draw the clip through the target anatomy to the desired position/tension. The needle advancer mechanism includes the needle 3 (shown in FIG. 13 and FIG. 14), a needle advancer pulley 19, anti-backdrive springs 20, a spring needle advance return 21, and a needle advancer arm 22. The needle 3 is advanced in a ratcheting motion facilitated by the needle advancer arm 22 which rocks in its channel within the two halves of the tool body, tool body right 1 and tool body left 2. The needle advancer pulley 19 is driven to move the needle advancer arm 22. Spring tabs on the needle advancer arm 22 (shown in FIG. 12) interface with the slots on the needle 3 (shown in FIG. 13) in order to achieve the ratcheting motion of the needle 3. The anti-backdrive springs 20 ensure that the needle 3 does not backdrive as the needle 3 advances.

In FIG. 11, the sequence of advancing the needle to deploy a clip is illustrated. The position of the needle 3 shown in FIG. 11, part A), is in the clip loading position. In this position, the hook at the back of the needle 3 is in line with the loop on the clip 10 which allows the needle 3 to pick up the clip 10 from the clip cartridge 12 when the needle 3 is advanced. In FIG. 11, part B), the needle 3 is advanced such that the tip has re-entered the tool tip and the clip 10 has been removed from the clip cartridge 12 and is following the needle 3 through the channel in the tool. As the needle 3 continues to progress in the clockwise direction as shown in FIG. 11, part C), an anti-backdrive on the needle 3 transfers from an anti-backdrive spring 20 at the top of the image to the anti-backdrive spring 20 at the middle of the image ensuring that the feature is always engaged through a full rotation. Continuing to advance the needle 3, the clip 10 has been pulled through the tissue and secured the tissue against the flat backing of the clip 10. Both tissues are then tensioned between the backing of the clip 10, and the face of the tool by continuing to advance the needle 3 until the appropriate tension is achieved, ensuring a proper seal to promote healing. The clasp 11 can then be deployed onto the clip 10, maintaining the tension in the repaired interface between the flat section of the clip 10 and the clasp 11. In FIG. 11, part D), the needle 3 is ready to repeat this sequence of operations.

The next mechanism in the sequence for deploying the clip is a clasping mechanism. Referring to FIG. 15 and FIG. 16, the clasp mechanism includes a clasp closer 23 and a clasp closer actuator pin 25. The clasp closer 23 is moved allowing the clasp closer actuator pin 25 to react against a slot cut into a clasp closure arm. With the clip 10 being held at the proper tension, the clasp 11 is pushed over the clip 10 as the clasp closure arm is closed. As the clasp 11 is advanced around the clip 10, it is forced into a portion in the tool, closing the clasp 11 and securing its position onto the clip 10. With the clasp 11 securing the tissue portions together, the clip 10 must now be released from the needle 3.

FIG. 17 is a cut away view of the tool at the point where the clasp 11 has just been applied to the clip 10. At this point, a clip cutter 17 is advanced towards a loop of the clip 10 that is held on a hook of the needle 3. The clip cutter 17 is applied a force to cut into a trailing section of the needle 3 by a clip cutter spring 18, shown in FIG. 7. The closed clip 10, clasp 11, and tissue can now be released from the tool. The needle 3 is then advanced using the needle advancement mechanism as described above until the hook on the needle 3 is in-line with an empty slot that is now in the clip cartridge.

Referring to FIG. 18, a cartridge advance mechanism 13 includes a clip cartridge advance mechanism body, such as the tool body right 1. The cartridge advance mechanism also includes a clip pusher spring 16 to apply a force to bias the clips 10 toward a ready position within the clip cartridge 12.

FIG. 19 illustrates a variation of a clipping apparatus tool tip 29, with zero to three additional degrees of freedom utilizing a tool shaft 26, a pitch joint 27, and a yaw joint 28. As shown in FIG. 7, the yaw joint is connected to a distal pivot mount 14, which is secured to the tool via a distal pivot mount screw 15. Degrees of freedom of the tool tip 29 are achievable with a combination of roll, pitch, and/or yaw mechanical joints or any other movable mechanisms in the tool shaft 26 between the tool tip 29 and either a power pack or a manual trigger handle, such as those described below.

An anastomosis clipping method sequence of operations is shown in FIG. 20 and FIG. 21 and includes, for example, the following steps: 1) orient the tool tip (and repeat as necessary throughout procedure) so that forceps are closed for entry through a trochar; 2) open the forceps; 3) position the tool tip around a first lumen; 4) close the forceps on the first lumen; 5) advance the needle through the first lumen; 6) open the forceps; 7) position the tool tip around a second lumen; 8) close forceps on the second lumen; 9) advance the needle through the second lumen; 10) further advance the needle to pull a clip through the first and second lumen; 11) lock the needle and forceps controls together; 12) advance the needle and move the forceps together to bring the clip to an upper arm of the forceps; 13) continue a motion of the needle and the forceps to close a clasp on the clip; 14) initiate a clip loop shear mechanism; 15) activate the clip loop shear mechanism; 16) retract the tool tip from the site of the clipping.

FIG. 22 shows an example of the engaged clip 10 and clasp 11 as it would appear deployed in surgical tissue to join lumen when creating an anastomosis.

An embodiment of a system provides the tool as an element of a shared control image guided fastening system for joining two deformable/moving sections of tissue. The system also includes a tissue fastening apparatus with associated fastening clips, positioning means for positioning the tissue fastening means at a fastening location, sensing means for tracking a desired fastening point, fastening location specification means to select one or more fastening points, illumination means for illuminating the fastening site, and computer processor means for controlling the operation of the positioning means at the said fastening means at the said specified one or more fastening sites. An overview of an illustrative system is provided in FIG. 23, which depicts a surgeon workstation 30, a vision system 31 (such as an endoscope), a robotic positioner 32, a power pack 33, a tool shaft 26, and a tool tip 29.

FIG. 24 shows a system block diagram of the system architecture and workstation/robotic workcell of the shared image-guided system. FIG. 25 shows an illustrated example of the robot-driven embodiment of the clipping apparatus with tool shaft 26 and tool tip 29, utilizing the robotic positioner 32, and power pack 33.

Another variation provides the clipping apparatus as a manual handheld surgical tool including a tissue fastening apparatus with associated fastening clips, a handheld trigger actuation system for human command of all apparatus actuations and to support manual positioning of the tissue fastening means. There is provided a method to fasten tissue using a flexible clip and clasp rather than traditional suturing, including the following manual steps of orienting the apparatus to the correct configuration to begin the sequence of fastening the tissue, advancing the apparatus needle and piercing the first piece of tissue to be fastened, further advancing the apparatus needle to secure the pierced tissue and moving the apparatus and attached tissue towards the second piece of tissue to be fastened, piercing the second piece of tissue to be fastened, advancing/retracting the apparatus needle to pull the clip through the holes in the two pieces of tissue being fastened, tensioning the clip and securing the clip with a clasp, releasing the clip and fastened tissue from the apparatus. See FIG. 26 for an illustration of the manual/handheld variation of the clipping apparatus showing the tool shaft 26 and the tool tip 29.

II. Second Illustrative Embodiment

In a second illustrative embodiment, FIG. 27 through FIG. 30 provide exterior views of a tool tip to highlight a general profile. The circular profile of the tool allows the tool to fit through a cannula port used during laparoscopic surgeries, while the tapered opening at the tip of the tool provides increased access to tissues. The tool tip includes two halves, a tool body left 100 and a tool body right 102, that encapsulate the internal mechanisms and are held together by two tool body screws 142. It should be noted that the tool is split for assembly reasons and could be secured together via other methods such as clips or tabs instead of the tool body screws 142.

The tool has been designed to deliver discrete clips through tissue and apply a clasp to secure the tissue together. The clip and clasp are shown in FIG. 31. The clip 114 is a flexible suture-like shape that consists of a loop on one end to hook onto a needle 104, and a flat wider tab at the other that stops the clip 114 from being pulled completely through the tissue. The clasp 119 is a flexible piece of polymer that has a latch molded into it such that when it is flexed over the clip 114, the latch engages and secures the clasp 119 around the clip 114, as shown in FIG. 31. The clip 114 and clasp 119 are made from a molded polymer that is biocompatible, and possibly also bioabsorbable, for surgical applications, but could also be made from a variety of other materials such as nylon or polypropylene depending on the intended use of the tool. The clip 114 and clasp 119 have been designed such that they are each loaded into reloadable cartridges which can then be loaded into the tool.

FIG. 32 shows a reloadable clip cartridge 115 which consists of eleven clips 114 housed in a clip cartridge inner housing 138 which then slides into a clip cartridge outer housing 137. A square raised feature on the inside of the clip cartridge outer housing 137 nests into a matching female recess on the clip cartridge inner housing 138 restricting the rotation of the inner housing relative to the outer housing. The clip cartridge 115 assembly is then secured together by a clip cartridge screw 136 as seen in FIG. 32. The loaded clip cartridge 115 can then be loaded into the tool ensuring that the empty position in the cartridge is located at an uppermost position as this will allow the needle 104 to be in any position when the cartridge is loaded.

Referring to FIG. 29 and FIG. 33, loading of the clip cartridge 115 into the tool is accomplished by first removing two clip cartridge cover screws 143 and a clip cartridge cover 103 from the tool body right 102. This provides access to the clip cartridge 115 as well as a clip cartridge advance mechanism body 116 which must be released from its locked position by removing a cartridge advancer positioning screw 144 (left) and sliding the clip cartridge advance mechanism body 116 back into the body of the tool compressing a clip cartridge advance mechanism compression spring 117. The cartridge advancer positioning screw 144 is then inserted into the rear locking (right) threaded hole in the tool body right 102 which secures the clip cartridge advance mechanism body 116 in the loading position. With the clip cartridge advance mechanism body 116 secured out of the way, the clip cartridges can then be slid back and removed through the port that was covered by the clip cartridge cover 103. Once the clip cartridge 115 is reloaded with clips, it is re-installed into the tool and the cartridge advancer positioning screw 144 is removed from the rear locking position allowing the clip cartridge advance mechanism body 116 to be repositioned back into the forward locked position where the cartridge advancer positioning screw 144 is returned to the forward locking position. The clip cartridge cover 103 and the two clip cartridge cover screws 143 are then re-installed into the tool.

FIG. 34 provides a detailed view of a clasp cartridge 107. The clasp cartridge 107 consists of a clasp cartridge cover 139 that houses eleven clasps 119 being contained by a clasp retaining tab 105. The clasp cartridge 107 is loaded onto the tool body left 101 by opening up a clasp closure arm 106 to the loading position to allow access for the cartridge and then securing the clasp cartridge 107 in place with a clasp cartridge screw 145. In the cut away view of FIG. 35, a clasp pusher 120 is pushed forwards against the clasps 119 by a clasp pusher spring 121 such that when the clasp retaining tab 105 is removed, the clasps 119 are pushed forward into the forward deployment position.

There are four main mechanisms contained within the tool tip that provide the functionality to deliver a clip and to perform the basic functions. These are:

1. A needle advancer;
2. A clasp applier;
3. A clip cutter; and
4. A clip cartridge advancer.

A needle advancer mechanism is detailed in FIG. 36 and FIG. 37. The needle advancer mechanism is used to position the clipping tool needle 104 such that both halves of the target anatomy may be captured. The needle advancer mechanism is then subsequently used to draw the clip through the target anatomy to the desired position/tension. Referring to FIG. 36, the needle advancer mechanism includes the needle 104, a needle advancer arm 108, a needle advancer actuator 109, a needle advancer pin 140, a spacer 110, needle tension springs 112, and set screws 113. The needle 104 is advanced in a ratcheting motion facilitated by the needle advancer arm 108 which rocks in its channel within the two halves of the tool body, tool body left 101 and tool body right 102, by linearly actuating the needle advancer actuator 109 in push and pull motions, shown at both extremes in FIG. 36. Spring tabs on the needle advancer arm 108 (shown in FIG. 38) interface with the slots on the needle 104 (shown in FIG. 39) in order to achieve the ratcheting motion of the needle 104. The needle tension springs 112 ensure that the needle 104 does not backdrive as the needle advancer actuator 109 rocks by applying friction to the needle 104. Sufficient preload on the needle tension springs 112 is achieved by adjusting the threaded depth of the set screws 113 (in two places).

In FIG. 37, the sequence of advancing the needle to deploy a clip is illustrated. The position of the needle 104 shown in FIG. 37, part A), is in the clip loading position. In this position, the hook at the back of the needle 104 is in line with the loop on the clip 114 which allows the needle 104 to pick up the clip 114 from the clip cartridge 115 when the needle 104 is advanced. In FIG. 37, part B), the needle 104 is advanced such that the tip has re-entered the tool tip and the clip 114 has been removed from the clip cartridge 115 and is following the needle 104 through the channel in the tool body left 101. As the needle 104 continues to progress in the clockwise direction as shown in FIG. 37, part C), an anti-backdrive on the needle 104 transfers from the needle tension springs 112 at the bottom of the image to the spring at the top ensuring that the feature is always engaged through a full rotation. Continuing to advance the needle 104 as shown in FIG. 37, part D), the clip 114 has been pulled through the tissue and secured the tissue against the flat backing of the clip 114. Both tissues are then tensioned between the backing of the clip 114, and the face of the tool by continuing to advance the needle 104 until the appropriate tension is achieved, ensuring a proper seal to promote healing. At that point, the clasp 119 can be deployed onto the clip 114, maintaining the tension in the repaired interface between the flat section of the clip 114 and the clasp 119.

The next mechanism in the sequence for deploying the clip is a clasping mechanism. Referring to FIG. 41, the clasp mechanism consists of the clasp closure arm 106, a clasp closer pin 123, clasp closer actuator 124, and a clasp closer actuator pin 140. The clasp closure arm 106 is pinned to the tool body left 101 and rotates about the clasp closer pin 123. To close the clasp closure arm 106, the clasp closer actuator 124 is moved in a linear motion allowing the clasp closer actuator pin 140 to react against the angled slot cut into the clasp closure arm 106 as shown in FIG. 41. As the clasp closer actuator 124 is retracted, the tip of the clasp closure arm 106 enters into the clasp cartridge 107 and contacts the clasp 119 that is positioned to be deployed.

Referring to FIG. 42, the tip of the clasp closure arm 106 is just beginning to contact the foremost clasp 119 in the clasp cartridge 107. With the clip 114 being held at the proper tension, the clasp 119 is pushed over the clip 114 as the clasp closure arm 106 is closed, as shown in FIG. 42. As the clasp 119 is advanced around the clip 114, it is forced into an anvil that is shaped into the tool body right 102, closing the clasp 119 and securing its position onto the clip 114. With the clasp 119 securing the tissue portions together, the clip 114 must now be released from the needle 104.

FIG. 43 is a cut away view of the tool at the point where the clasp 119 has just been applied to the clip 114. At this point, a clip cutter 111 is advanced towards a loop of the clip 114 that is held on a hook of the needle 104. The clip cutter 111 runs against and is directed by a flat surface cut into a trailing section of the needle 104 (shown in FIG. 40).

Also shown in FIG. 43, the clip cutter 111 shears the loop of the clip 114 against the needle 104. The closed clip 114, clasp 119, and tissue can now be released from the tool by opening the clasp closure arm 106 and repositioning the tool away from the site that has been clipped, allowing the tissue to freely release from the tool, taking with the tissue the clip 114 and clasp 119. The needle 104 is then advanced using the needle advancement mechanism as described above until the hook on the needle is in-line with an empty slot that is now in the clip cartridge. This position is shown in FIG. 49, which illustrates all of the components in the cartridge advancement mechanism as well as the sequence of events that occur when advancing the clip cartridge 115.

Referring to FIG. 44 through FIG. 47, the cartridge advance mechanism consists of the clip cartridge advance mechanism body 116, a clip cartridge advance mechanism compression spring 117, clip cartridge advance actuator 118, clip cartridge advance mechanism extension spring 125, cartridge advancer pin 126, clip cartridge advance mechanism shoulder bolt 127, pawl housing 128, pawl 129, pawl pin 130, pawl spring pin 131, pawl spring 132, detent shaft 133, detent pin 134, and a detent spring 135.

A sequence of advancing the clip cartridge 115 begins in FIG. 48, part A). As the clip cartridge advance actuator 118 is retracted, the cartridge advancer pin 126 reacts against an angled slot in the pawl housing 128 causing the housing to begin rotating about the clip cartridge advance mechanism shoulder bolt 127 that is secured into the clip cartridge advance mechanism body 116. In FIG. 48, part B), the pawl housing 128 has rotated such that the pawl 129 contacts a rotation feature on the back of the clip cartridge 115 (refer to FIG. 32 for a detailed view of these features). As the clip cartridge advance actuator 118 continues to retract and rotate the pawl housing 128, the pawl 129 rotates the clip cartridge 115 forward one slot, presenting the next clip 114 to the needle 104 as seen in FIG. 48, part C). FIG. 48, part D) shows how the cartridge advance mechanism resets to a home position. When the clip cartridge advance actuator 118 is advanced, the pawl housing 128 begins to rotate back towards the home position while being assisted by the clip cartridge advance mechanism extension spring 125. As the pawl housing 128 is returning, the pawl 129 drags across the back of the clip cartridge 115, causing the pawl 129 to rotate about the pawl pin 130. As the pawl 129 rotates in the pawl housing 128, the pawl spring 132 (held in place by the pawl spring pin 131) is compressing until the point where the pawl 129 can slide past the rotation feature on the back of the clip cartridge 115 and return to the initial position shown in FIG. 48, part A).

To help lock each position containing a clip 114 in the clip cartridge 115, a detent shaft 133 is used, as shown in FIG. 49. Within the clip cartridge advance mechanism body 116 the detent shaft 133 compresses the detent spring 135 and is held in place by the detent pin 134. The back of the clip cartridge 115 (refer to FIG. 32 for detailed view of these features) has the detent feature at each clip 114 position that the detent shaft 133 locks into and is forced out of as the pawl 129 rotates the clip cartridge 115. FIG. 49, part A) illustrates the position with the detent shaft 133 locked into the detent of the clip cartridge 115, while FIG. 49, part B) shows the intermediate state while the clip cartridge 115 is rotating between positions. Detent spring 135 provides enough force to allow the detent shaft 133 to hunt for the detent, and as a rounded tip of the detent shaft 133 finds the detent it will be forced into it and locks the position as shown in FIG. 49, part C).

FIG. 50 illustrates a variation of a clipping apparatus tool tip 149, with zero to three additional degrees of freedom utilizing a tool shaft 146, a pitch joint 147, and a roll joint 148. This would be achieved with a combination of roll, pitch, and/or yaw mechanical joints in the tool shaft between the tool tip 149 and either a power pack or a manual trigger handle, such as those discussed above.

FIG. 51 shows an illustration of an operations flow of a mechanical actuation system to deploy the clip in the tissue. In Step 1, the needle is partially advanced (pulling attached tension clip) and pierces a first thickness of tissue of a target lumen. In Step 2 the partially advanced needle is further advanced and pierces a second thickness of tissue of the target lumen, followed by a complete (360 degree) needle rotation within the tool tip in Step 3. In Step 4, the device deploys a tension clip with an engaged clasp, and the clip-clasp complex is released from the tool tip. In one embodiment, the mechanical actuation system includes a curved needle, and the actuation mechanism to drive the needle with an attached clip through the tissue, a clasp-tightening mechanism, and a clasp closing and severing mechanism. In this embodiment, the tissue fastening method would use a half-loop clip that does not fully close in a 360 degree circle. In both embodiments of the apparatus there is provided a means to orient and position the clip-actuation system including one or more rotational joints on the tool shaft, and transmission means for relaying the actuation of the clip actuation mechanism from the shaft through the rotational joints.

An anastomosis fastening method and sequence of operations is shown in FIG. 52, and includes, for example, the following steps: 1.0) orient the tool tip (and repeat as necessary throughout procedure); 2.0) approximate the tissue of the lumen to be joined; 3.0) partially advance the needle mechanism; 4.0) pierce the first lumen; 5.0) partially advance the needle mechanism; 6.0) move the tool tip (that has already pierced the first lumen) towards the second lumen; 7.0) pierce the second lumen; 8.0) finish advancing the needle mechanism; 9.0) deploy the tension clip, and adjust the clip diameter as necessary; 10.0) secure the clip with the interlocking clasp; 11.0) release the engaged clip and clasp from the tool tip; 12.0) advance the clip cartridge; and 13.0) reset the apparatus to prepare for the next clipping sequence.

The second embodiment of the clipping tool may be used in a fastening method as described above with respect to the first embodiment, and used as an element of a shared control image-guided fastening system, as discussed above in relation to FIG. 23. Additionally, the third embodiment of the clipping tool may be incorporated in a manual handheld surgical tool, as discussed above in relation to FIG. 26.

III. Third Illustrative Embodiment

The basic device according to a third embodiment includes a tool tip mechanism that includes a curved needle made from a shape memory alloy. The needle begins in a straight configuration within the tool and is advanced inside a needle guide through the clasp of a suture-like clip. The needle is then further advanced out of the needle guide and begins to curve, and in several stages pierces the first and second thicknesses of target tissue. After piercing the two pieces of tissue of a tubular structure (called a "lumen"), the needle fully advances until the tip curves 180 degrees and reenters the tool tip, where it catches the end of the clip and pulls it through the two layers of target tissue and the clasp. The apparatus then tensions the clip, closes the clasp, and releases the engaged full-loop clip from the tool tip allowing the needle to return to its initial position and engage a new clip for the next deployment.

The tool tip described herein has been conceived to quickly deploy a fastening clip to oppose two pieces of tissue for the purposes of relieving the surgeon of the challenging task of tying interrupted sutures during a laparoscopic procedure. The embodiment of this tool can also be extended for use during open procedures and should not be limited to laparoscopic procedures. Furthermore, this tool should not be limited to only fastening tissues, however it should be considered for use in any procedure where two articles are to be fastened together utilizing the superelastic nature of a reciprocating shape memory alloy curved needle to deploy a series of clips from a reloadable cartridge.

A method of piercing the tissue and delivering the clip through the tissue is accomplished through the use of a superelastic shape memory alloy needle with the preferred needle material being nitinol. The superelastic needle is preformed and annealed into a curved profile allowing it to be deformed into a straight orientation and then takes the preformed curved path with little to no plastic deformation as the needle is advanced out of a guiding sheath. The two major benefits of the curved path are first, that the curved profile mimics the path of the current curved needles that surgeons use to suture tissues, and second, the path reintroduces the tip of the needle back to the distal tip of the tool where the needle picks up the tip of the clip from the clip cartridge.

To accomplish the basic functions outlined above to deliver a clip using the tool tip described herein, the tool tip must be attached to a positioning mechanism. This positioning device can be attached to a solid tool shaft or can also be incorporated with additional degrees of freedom to increase maneuverability of the tool tip. FIG. 53 shows a tool tip 218 attached to a tool shaft 216 that is entered into the body via a cannula with two additional degrees of freedom added. Providing a first degree of freedom is a pitch joint 215, followed by a roll joint 214, providing a full range of motion for positioning a shape memory alloy needle 201 at an end of the tool tip 218.

FIG. 54 is a close up of the tool tip 218 in a configuration that is ready to capture the tissue that will be clipped together. As shown, a clip cartridge 206 is attached to a tool body 205 with the shape memory alloy needle 201 being guided by a needle guide 204 protruding through the clip cartridge 206. The needle guide 204 is a straight section of stainless steel tube used to straighten the curved shape memory alloy needle 201 when it is retracted into the needle guide 204.

FIG. 55 shows the details of the shape memory alloy needle 201 as it exists in its annealed, relaxed state. The superelastic nature of the alloy provides a very unique characteristic compared to other metals. Superelastic shape memory alloy has a very high capacity for allowing a very large strain while remaining in the elastic region of the stress-strain curve. This characteristic allows the shape memory alloy needle 201 to be straightened from its curved shape as it is retracted into the needle guide 204, and takes the curved path as it is advanced out of the needle guide 204, returning the tip of the needle to the same position. The tip of the shape memory alloy needle 201 is notched, as shown in FIG. 55, to engage the loop on a clip 202 when it is being held in the clip cartridge 206.

FIG. 56 shows the details of the clip 202 and a clasp 203. The clip 202 and the clasp 203 are made from a molded polymer that is biocompatible, and could also be bioabsorbable for a surgical application, but could be made from a variety of other materials such as nylon or polypropylene depending on the intended use of the tool. The clip 202 has a loop at one end for the shape memory alloy needle 201 to pick up on, while the other end has half of a clasping feature molded into it. The clasping feature consists of two prongs that will rest on the clasp 203 to maintain a gap for the shape memory alloy needle 201 and the needle guide 204 to pass through when the needle is being deployed as seen in FIG. 56. At the appropriate time in the deployment sequence, the prongs on the clip 202 are pressed over the clasp 203, securing the clasp 203 around the main section of the clip 202 as shown in FIG. 56.

FIGS. 57A to 57J demonstrate a sequence of operations within the tool to accomplish the basic functions listed above. Shown in FIG. 57A, sequence 1, the tool tip 218 has been loaded with the clip cartridge 206 and has the shape memory alloy needle 201 retracted into the needle guide 204 which is in the cartridge loading position. In this configuration, the tool can be entered into the body through a cannula and positioned in the proximity of the tissues to be clipped together. If required, this configuration allows the rounded tip of the tool tip 218 to be used to manipulate other surrounding tissues or organs without the worry of causing any residual damage.

FIG. 57B, sequence 2, shows the tool positioned near the tissues to be joined and the needle guide 204 and shape memory alloy needle 201 are advanced between the opening of the clip 202 and clasp 203. Both the clip 202 and clasp 203 are held in position by a clip cartridge inner housing 208 and maintain their gap by the prongs of the clip 202 resting on the clasp 203 as illustrated in FIG. 56.

As shown in FIG. 57C, sequence 3, the shape memory alloy needle 201 can be advanced out of the needle guide 204, allowing the shape memory alloy needle 201 to begin to return to its no-strain preformed curved shape. At this stage, the tool is ready to capture the first piece of tissue 213. The tool tip is positioned by insertion depth and articulation of joints 214 and 215 in a similar way to how a surgeon would pierce the tissue using conventional curved needles to capture the first piece of tissue to be joined. With the first piece of tissue perforated by the shape memory alloy needle 201, the second piece of tissue can be captured as shown in FIG. 57D, sequence 4. It is important to pierce the tissue 213 at the location where the clip is to be placed, as the shape memory alloy needle 201 will draw the clip back through the holes created by the needle.

FIG. 57E, sequence 5, illustrates that once the second fold of tissue 213 is captured, the shape memory alloy needle 201 is then advanced further out of the needle guide 204. As the needle continues to advance and take the remainder of the un-strained preformed curve, the tip of the needle re-enters the clip cartridge 206 via the opening in a clip cartridge cover 207. The tip of the shape memory alloy needle 201 then travels through the loop on the clip 202 being held in the clip cartridge inner housing 208, allowing the notch in the needle to engage the loop. As the needle is then retracted into the needle guide 204, the clip 202 is pulled out of the clip cartridge inner housing 208 and follows the path of the needle as it retracts back through the tissue 213 as shown in FIG. 57F, sequence 6, (note that the clip in FIGS. 57F and 57G, sequences 6 and 7, does form out of the cross sectional plane).

FIG. 57G, sequence 7, shows the shape memory alloy needle 201 retracted to a straight configuration within the needle guide 204 and the clip 202 pulled through the tissue 213. As the clip is pulled through the tissue, the free length of clip that is contained within the clip cartridge inner housing 208 is free to pull through the slot at the front of the clip cartridge cover 207. Each clip 202 is packaged into the clip cartridge inner housing 208 sequentially in the reverse order that they will be used by the tool to ensure that they are free to be removed without becoming entangled with the other clips.

FIG. 57H, sequence 8, shows that with the shape memory alloy needle 201 in a straight configuration due to the needle guide 204, one end of the clip 202 is pulled through the opening for the clasp 203 by retracting both the shape memory alloy needle 201 and needle guide 204 together. By pulling the free length of the clip 202 through the clasp 203, the tissue 213 becomes contained by the clip 202. At this point, the shape memory alloy needle 201 and needle guide 204 are retracted to tension the clip 202 around the tissue 213 similar to a surgeon tightening a knot using manual suture techniques.

FIG. 57I, sequence 9, shows the method of securing the clasp 203 around the clip 202 through the actuation of a clasp closer arm 209. With the proper tension applied to the clip 202, the clasp 203 is closed around the main body of the clip 202 to maintain the tension on the tissue once the clip 202 is released from the tool. Closing the clasp 203 is accomplished by rotating the clasp closer arm 209 towards the top of the clasping feature that is molded into the end of the clip 202. As the clasp closer arm 209 rotates down, the curved profile at the tip engages the rounded top of the clasp feature and forces the prongs on the clip 202 down over the clasp 203, locking the two pieces together over the body of the clip 202. The clasp closer arm 209 is then returned to its stored position.

The clip and tissue must now be released from the tool which is accomplished as shown in FIG. 57J, sequence 10. To release the clip from the needle, the loop on the clip 202 is sheared from the notch in the shape memory alloy needle 201 by advancing the needle guide 204 relative to the shape memory alloy needle 201. As seen in FIG. 15, a shear 219 is cut into a single quadrant of the needle guide 204 and provides a single location where the loop of the clip 202 is sheared against the notch of the shape memory alloy needle 201. With the loop split, the clip 202 and tissue are free to release from the tool and the tool can be re-positioned to the next location where a clip is to be deployed. The clip cartridge inner housing 208 is then cycled to the next position by a cartridge advance mechanism 212 which is shown in FIG. 58. For each position that contains a clip within the clip cartridge 206, there is an advancement notch and detent on the back of the clip cartridge inner housing 208 that a detent shaft 211 engages and disengages by a simple compression spring. The features on the back of the clip cartridge inner housing 208 are also shown in FIG. 58.

Loading of the clip cartridge 206 is shown in FIG. 58. The clip cartridge 206 is made of two parts, the clip cartridge cover 207 and the clip cartridge inner housing 208 that nest into each other. Each clip 202 and clasp 203 are individually loaded into the clip cartridge inner housing 208 with the loop of the clip 202 being held directly across from the location that the clip 202 and clasp 203 are secured in the clip cartridge inner housing 208, as shown in FIG. 58. As stated previously, each clip is loaded sequentially in the reverse order that they will be deployed by the tool to avoid entanglement with each other when they are deployed. Once the clip cartridge inner housing 208 is fully loaded, the clip cartridge cover 207 slides over the clip cartridge inner housing 208 creating the clip cartridge 206 that is now loaded onto the tool body 205. The clip cartridge 206 is then secured onto the tool body 205 and ready to be used.

The third embodiment of the clipping tool may be used in any of the fastening methods described above, and used as an element of a shared control image-guided fastening system, as discussed above in relation to FIG. 23. Additionally, the third embodiment of the clipping tool may be incorporated in a manual handheld surgical tool, as discussed above in relation to FIG. 26.

In all illustrative embodiments of the apparatus there is provided a way to orient and position the clip-actuation system. In one example, one or more rotational joints on the tool shaft may be used, along with a transmission device for relaying the actuation of the clip actuation mechanism from the shaft through the rotational joints.

The foregoing disclosure describes merely illustrative embodiments of the present invention. As will be understood by those skilled in the art, the present invention may be embodied in other specific forms without departing from the spirit or essential characteristics thereof. Accordingly, the disclosure is intended to be illustrative of the present invention, but not limiting of the scope of the invention, as well as the following claims. The disclosure and any discernible variants of the teachings herein define, at least in part, the scope of the claim terminology, such that no inventive subject matter is dedicated to the public.

The invention claimed is:

1. A tool to fasten tissue portions or to fasten a prosthetic element to tissue, comprising:
   a gripper to hold one or more portions of tissue;
   a needle;
   an actuator to drive the needle;
   a fastener cartridge to store one or more tissue fasteners;
   a holder cartridge to store one or more holders; and
   a holder applier to secure one of the holders on one of the fasteners, wherein
   the actuator drives the needle so that the needle pulls a first fastener of the one or more tissue fasteners from the fastener cartridge, the actuator drives the needle through the one or more portions of tissue held by the gripper to form a hole in the one or more portions of tissue, the needle pulls a leading portion of the first fastener through the hole without a trailing portion of the first fastener being pulled through the hole, and the holder applier secures a first holder of the one or more holders from the holder cartridge onto the leading portion of the first fastener.

2. The tool according to claim 1, further comprising:
   a cutter to cut one of the fasteners, and the cutter cuts off a front end of the leading portion of the first fastener that protrudes from the first holder that is secured onto the first fastener.

3. The tool according to claim 1, wherein the one or more fasteners include at least one of a clip, a staple, and a T-suture.

4. The tool according to claim 1, wherein the one or more holders include at least one of a clasp, a stopper, and a clamp.

5. The tool according to claim 1, wherein the one or more fasteners and the one or more holders are made of at least one of a polymer material, a bioabsorbable material, and a biocompatible material.

6. The tool according to claim 1, wherein the actuator drives the needle around a 360° advancement path.

7. The tool according to claim 1, wherein the gripper includes two arms, and at least one of the two arms is a curved arm that is movable.

8. The tool according to claim 1, further comprising:
   a fastener advancing mechanism to advance a second fastener to a ready position to be pulled by the needle after the first fastener is pulled from the fastener cartridge.

9. The tool according to claim 1, further comprising:
   a holder advancing mechanism to advance a second holder to a ready position to be applied by the holder applier after the first holder is removed from the holder cartridge by the holder applier.

10. The tool according to claim 1, further comprising:
    a tool tip body that includes the gripper, the needle, the actuator, the fastener cartridge, the holder cartridge, and the holder applier;
    a shaft; and
    a mechanism to join the tool tip body to the shaft, the mechanism allowing the tool tip body to be movable with at least two degrees of freedom.

11. A manual handheld device to fasten tissue portions or to fasten a prosthetic element to tissue, comprising the tool according to claim 1.

12. A system to perform a surgical procedure, comprising:
    the tool according to claim 1;
    a positioning device to position the tool at a tissue fastening location;
    a sensor to detect a desired tissue fastening point;
    a fastening location specification unit to select one or more tissue fastening points;
    an illumination device to illuminate the fastening location; and
    a controller to control operation of the tool and the positioning device.

13. A method to fasten tissue using the tool according to claim 1, comprising:
    orienting the tool to a configuration to begin a sequence of fastening the tissue;
    gripping a first piece of the tissue to be fastened with the gripper of the tool;
    advancing the needle of the tool to pierce the first piece of the tissue to be fastened;
    opening the gripper while the needle remains pierced through the first piece of the tissue to be fastened;
    gripping a second piece of the tissue to be fastened with the gripper;
    further advancing the needle to pierce the second piece of the tissue to be fastened;
    advancing the needle to pull the leading portion of the first fastener stored in the tool through pierced holes in the first and second pieces of the tissue without the trailing portion of the first fastener being pulled through the pierced holes; and
    securing the first holder stored in the tool onto the leading portion of the first fastener with the holder applier of the tool.

14. The method according to claim 13, further comprising:
    tensioning the first fastener by advancing the needle to pull the first fastener before securing the fit holder.

15. The method according to claim 13, further comprising:
    cutting a front end of the leading portion of the first fastener that protrudes from the first holder that is secured onto the first fastener.

16. A tool to fasten tissue portions or to fasten a prosthetic element to tissue, comprising:
    a gripper to hold one or more portions of tissue;
    a needle;
    an actuator to drive the needle;
    a fastener cartridge to store one or more tissue fasteners;
    a holder cartridge to store one or more holders; and
    a holder applier to secure one of the holders on one of the fasteners, wherein
    the actuator drives the needle so that the needle pulls a first fastener of the one or more tissue fasteners from the fastener cartridge, the actuator drives the needle through the one or more portions of tissue held by the gripper to form a hole in the one or more portions of tissue, the needle pulls a leading portion of the first fastener through the hole without a trailing portion of the first fastener being pulled through the hole, and the holder applier secures a first holder of the one or more holders from the holder cartridge onto the leading portion of the first fastener, and wherein
    the needle is a curved needle.

17. A tool to fasten tissue portions or to fasten a prosthetic element to tissue, comprising:
    a gripper to hold one or more portions of tissue;
    a needle;
    an actuator to drive the needle;
    a fastener cartridge to store one or more tissue fasteners;

a holder cartridge to store one or more holders; and a holder applier to secure one of the holders on one of the fasteners, wherein the actuator drives the needle so that the needle pulls a first fastener of the one or more tissue fasteners from the fastener cartridge, the actuator drives the needle through the one or more portions of tissue held by the gripper to form a hole in the one or more portions of tissue, the needle pulls a leading portion of the first fastener through the hole without a trailing portion of the first fastener being pulled through the hole, and the holder applier secures a first holder of the one or more holders from the holder cartridge onto the leading portion of the first fastener, and wherein the needle includes a piercing end and an opposing end that includes a hook to pull a loop at a front end of the leading portion of the first fastener.

* * * * *

UNITED STATES PATENT AND TRADEMARK OFFICE
CERTIFICATE OF CORRECTION

PATENT NO. : 9,820,744 B2  
APPLICATION NO. : 14/038192  
DATED : November 21, 2017  
INVENTOR(S) : Axel Krieger et al.

Page 1 of 1

It is certified that error appears in the above-identified patent and that said Letters Patent is hereby corrected as shown below:

On the Title Page

Item (72), the third inventor's country, and the fourth inventor's country and city are incorrect. Item (72) should read:
-- (72) Inventors: Axel Krieger, Washington, DC (US);
                Peter Kim, Washington, DC (US);
                Chris Wilson, Port Perry (CA);
                Stephen Abellera, Scarborough (CA) --

Signed and Sealed this
Fourth Day of June, 2019

Andrei Iancu
*Director of the United States Patent and Trademark Office*